United States Patent [19]

Imazaki et al.

[11] Patent Number: 4,935,408
[45] Date of Patent: Jun. 19, 1990

[54] ORGANOTIN COMPOUNDS AND PESTICIDES CONTAINING THEM

[75] Inventors: Hideyuki Imazaki; Masazumi Fujikawa, both of Osaka; Katsuaki Oba, Shiga; Fusaharu Kumayama, Mie; Toshio Takahashi, Hyogo, all of Japan

[73] Assignees: Shionogi & Co., Ltd.; Nitto Kasei Co., Ltd., both of Oaska, Japan

[21] Appl. No.: 191,058

[22] Filed: May 6, 1988

Related U.S. Application Data

[62] Division of Ser. No. 898,688, Aug. 21, 1986, Pat. No. 4,774,235.

[30] Foreign Application Priority Data

Sep. 3, 1985 [JP] Japan .................. 60-195355

[51] Int. Cl.$^5$ .................. C07F 7/22; A01N 55/06
[52] U.S. Cl. .................. 514/63; 514/95; 514/109; 514/189; 514/493; 556/12; 556/25; 556/24; 556/32; 556/38; 556/84; 556/86; 556/88; 556/94; 544/181; 549/3; 548/103
[58] Field of Search .................. 556/12, 25, 24, 38, 556/32, 94, 88, 86, 84; 514/493, 109, 189, 63, 95; 544/181; 548/103; 549/3

[56] References Cited

U.S. PATENT DOCUMENTS

| | | | |
|---|---|---|---|
| 3,448,131 | 6/1969 | Chan et al. | 556/88 X |
| 3,476,472 | 10/1969 | Suzuki et al. | 556/86 |
| 3,634,479 | 1/1972 | Ridenour et al. | 556/24 X |
| 3,657,451 | 4/1972 | Horne | 514/493 |
| 3,677,738 | 7/1972 | Minieri | 514/493 X |
| 3,789,057 | 1/1974 | Reifenberg et al. | 556/94 X |
| 3,892,863 | 7/1975 | Kushlefsky et al. | 514/493 |
| 3,923,998 | 12/1975 | Gitlitz | 514/493 |
| 3,969,386 | 7/1976 | Ballard et al. | 556/12 |
| 3,971,539 | 10/1969 | Suzuki et al. | 556/84 |
| 4,010,276 | 3/1977 | Gitlitz | 514/493 |
| 4,058,545 | 11/1977 | Gitlitz | 556/86 X |
| 4,326,798 | 4/1982 | Gitlitz et al. | 514/493 |
| 4,343,815 | 8/1982 | Gitlitz | 514/493 |
| 4,703,059 | 10/1987 | Kano et al. | 514/493 |

FOREIGN PATENT DOCUMENTS 0116224 11/1974 Japan ................. 556/12

Primary Examiner—Paul F. Shaver
Attorney, Agent, or Firm—Wenderoth, Lind & Ponack

[57] ABSTRACT

A compound of the formula:

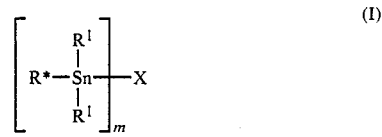

in which $R^1$ represents alkyl, cycloalkyl or aralkyl, $R^*$ represents fluorophenyl or trifluoromethylphenyl when $R^1$ is alkyl; $R^*$ represents dichlorophenyl, neopentyl, trimethylsilylmethyl, dimethylphenylsilylmethyl or a group of the formula:

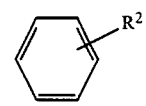

wherein $R^2$ represents halogen, trifluoromethyl, lower alkyl or lower alkoxy when $R^1$ is cycloalkyl; or $R^*$ represents 2-thienyl, 3-thienyl, neopentyl, trimethylsilylmethyl, dimethylphenylsilylmethyl or a group of the formula:

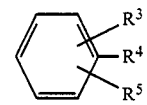

wherein $R^3$, $R^4$ and $R^5$ independently represent halogen, trifluoromethyl, lower alkyl or lower alkoxy when $R^1$ is aralkyl, m represents 1 or 2, and X represents halogen, imidazolyl, triazolyl, phenylthio or a radical selected from the group consisting of:

—OCOR$^6$, —SSCNR$^7$R$^8$, —NCO, —NCS.

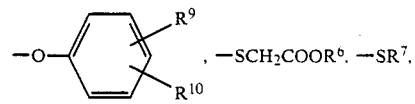

, —SCH$_2$COOR$^6$, —SR$^7$,

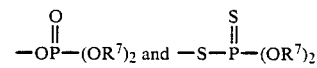

wherein $R^6$ represents alkyl, $R^7$ and $R^8$ independently represent lower alkyl and $R^9$ and $R^{10}$ independently represent hydrogen or lower alkyl when m is 1; or they independently represent oxygen, sulfur or a radical selected from:

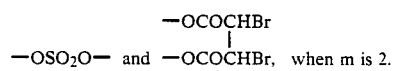

A process for preparing the compound (I) and a pesticidal composition containing the compound (I) are also provided.

2 Claims, No Drawings

ORGANOTIN COMPOUNDS AND PESTICIDES CONTAINING THEM

This is a Rule 60 Divisional application of Ser. No. 898688, filed Aug. 21, 1986 now Pat. No. 4774235.

This invention relates to novel asymmetric triorganotin compounds, to their preparation and to pesticidal compositions containing the novel compounds.

There exist a wide variety of pests which are parasitic on plants. Among them, mites (Acarina) do considerable damage to a wide range of crops and garden plants, which causes a serious problem in agricultural management. Since such phytophagous mites rapidly acquire a tolerance to pesticides, novel and efficient pesticides have continuously been sought.

Organic compounds which are known to be useful for controlling such mites include, for example, cyhexatin (Plictran ®, U.S. Pat. No. 3,264,177) and fenbutatin oxide (Osadan ®, U.S. Pat. No. 3,657,451). However, such known compounds have drawbacks that their pesticidal activities varies depending on species of pests, and that they do not inhibit a certain species of spider mites because of the acquired tolerance.

In view of the above, the present inventors have made extensive study on organotin compounds in order to find effective compounds exhibiting pesticidal activity, in particular, those effective to the spider mites which have already acquired a tolerance against the existing pesticides. As a result of the study, it has been found that the asymmetric triorganotin compounds of the formula (I) below exhibit an excellent pesticidal activity, in particular, to the spider mites exhibiting tolerance against the known organotin compounds.

Thus, the present invention provides assymmetric triorganotin compounds having pesticidal activity of the formula (I):

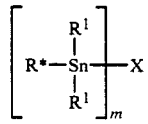
(I)

in which $R^1$ represents alkyl, cycloalkyl or aralkyl, $R^*$ represents fluorophenyl or trifluoromethylphenyl when $R^1$ is alkyl; $R^*$ represents dichlorophenyl, neopentyl, trimethylsilylmethyl, dimethylphenylsilylmethyl or a group of the formula:

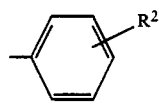

wherein $R^2$ represents halogen, trifluoromethyl, lower alkyl or lower alkoxy when $R^1$ is cycloalkyl; or $R^*$ represents 2-thienyl, 3-thienyl, neopentyl, trimethylsilylmethyl, dimethylphenylsilylmethyl or a group of the formula:

wherein $R^3$, $R^4$ and $R^5$ independently represent hydrogen, halogen, trifluoromethyl, lower alkyl or lower alkoxy when $R^1$ is aralkyl, m represents 1 or 2, and X represents halogen, imidazolyl, triazolyl, phenylthio or a radical selected from the group consisting of:

$-OCOR^6$, $-SSCNR^7R^8$, $-NCO$, $-NCS$,

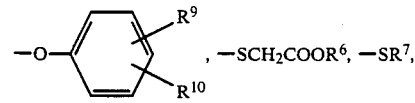, $-SCH_2COOR^6$, $-SR^7$,

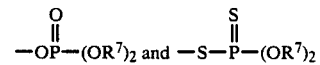

wherein $R^6$ represents alkyl, $R^7$ and $R^8$ independently represent lower alkyl and $R^9$ and $R^{10}$ independently represent hydrogen or lower alkyl when m is 1; or they independently represent oxygen, sulfur or a radical selected from:

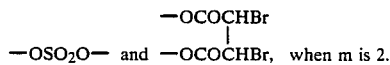

For purposes of the present invention, as disclosed and claimed herein, the following terms are as defined below.

The term "alkyl" refers to a straight or branched saturated hydrocarbon radical having one to twelve carbon atoms, including methyl, ethyl, propyl, isopropyl, butyl, isobutyl, sec-butyl, tert-butyl, pentyl, isopentyl, tert-pentyl, neopentyl, 1-methylbutyl, 1,2-dimethylbutyl, hexyl, heptyl, octyl, nonyl, decyl, and the like.

The term "lower alkyl" refers to an alkyl radical having less than six carbons, of the above defined alkyl.

The term "aralkyl" refers to an alkyl substituted by an aryl radical and includes benzyl, phenylethyl, phenylpropyl, methylbenzyl, neophyl, and the like.

The term "cycloalkyl" refers to a saturated hydrocarbon ring having three to ten carbon atoms, such as cyclopropyl, cyclobutyl, cyclopentyl, cyclohexyl, cycloheptyl, cyclooctyl, cyclononyl, cyclodecyl, and the like.

The term "halogen" means chloro, bromo, iodo and fluoro.

The term "pests" herein used should be considered to mean both insects and mites harmful to plants, especially phytophagous ones, and, the term "pesticides" or "pesticidal composition" to include insecticides and acaricides.

The process for the preparation of the compounds of the formula (I) will be detailed below.

The compounds (I) wherein X is halogen, which will hereinafter be referred to as compound (Ia), can be prepared according to the following Reaction Scheme I, whereas the other compounds (I) wherein X is other than halogen can be prepared from the compounds (Ia) according to the Reaction Schemes II to IV hereinafter described.

Reaction Scheme I

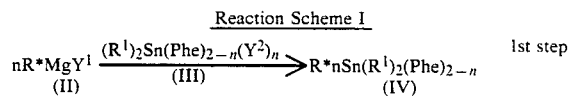

1st step

-continued
Reaction Scheme I

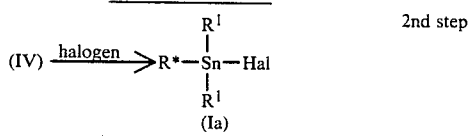 2nd step

In the above scheme, R* and $R^1$ are as previously defined, Hal, $Y^1$ and $Y^2$ are each chlorine, bromine or iodine, and n is 1 or 2, with the proviso that when n is 1, R* is a silicon-containing group and when n is 2, R* is an aryl or neopentyl group. The reactions are detailed below.

1st step

A compound (II) is reacted with an organotin halide (III) at a temperature from about 5° C. to 100° C. in a suitable solvent to yield an asymmetric tetraorganotin compound of the general formula (IV). Preferred solvents are ethers such as diethyl ether, dibutyl ether, tetrahydrofuran and the like.

The starting compound (II) may be conventionally prepared under the conditions usually employed for the preparation of a Grignard reagent.

The starting organotin halide of the general formula (III) wherein n is 2 can be represented by the formula:

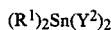

and may be prepared by redistribution reaction between a corresponding symmetric tetraorganotin compound of the formula:

wherein $R^1$ is as defined above, and a stannic halide according to known procedures. The asymmetric phenyldiorganotin halide, which corresponds to the starting compound of the formula (III) wherein n equals to 1 and has the formula:

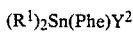

is itself an objective compound of the present invention and, therefore, may be prepared from the aforementioned starting compound (III) wherein n is 2, in accordance with the Reaction Scheme I.

2nd step

Halogenation of the asymmetric tetraorganotin compound of the formula (IV) is convertionally carried out by direct addition of a gaseous halogen, or by addition of halogen dissolved in a suitable solvent, to a solution of the asymmetric tetraorganotin compound dissolved in the same solvent, while maintaining the reaction temperature at $-50°$ C. to 30° C. Suitable solvents employed in the reaction include chloroform, carbon tetrachloride, benzene, toluene, heptane, hexane, and the like. Chloroform and carbon tetrachloride are especially preferred.

A preferred molar ratio of the asymmetric tetraorganotin compound (IV) and halogen is about 1:1. The reaction temperature is preferably maintained in the range of $-10°$ C. to 10° C.

The reaction terminates when the addition of halogen or a halogen solution is complete. The reaction mixture is concentrated, and the desired compound is separated and purified by recrystallization, vacuum distillation or column chromatography, if necessary. The asymmetric triorganotin halides (Ia) thus prepared are liquid or solid at room temperature.

These halides (Ia) are easily converted to other objective compounds (I) of the invention, such as hydroxides, bis(asymmetric triorganotin)oxides and other various derivatives as shown in the following Reaction Schemes, by known procedures.

Reaction Scheme II

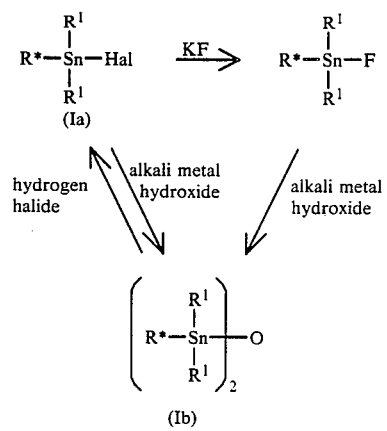

Reaction Scheme III

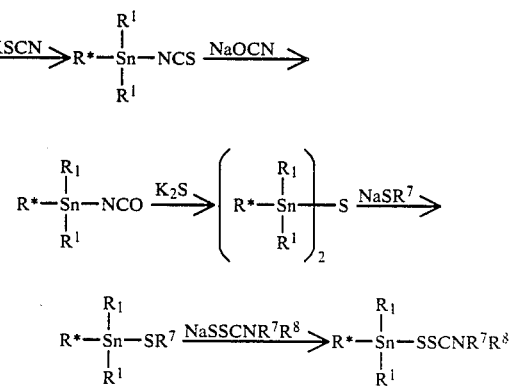

Reaction Scheme IV

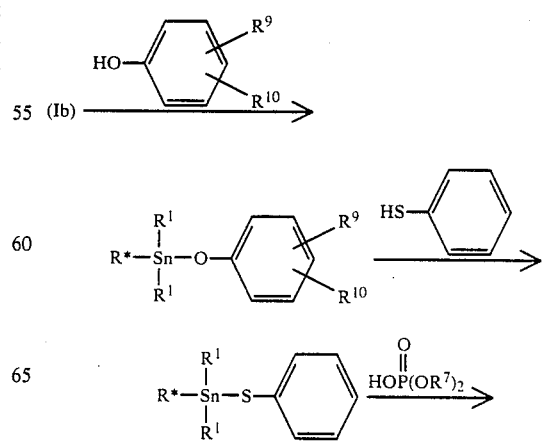

-continued
Reaction Scheme IV

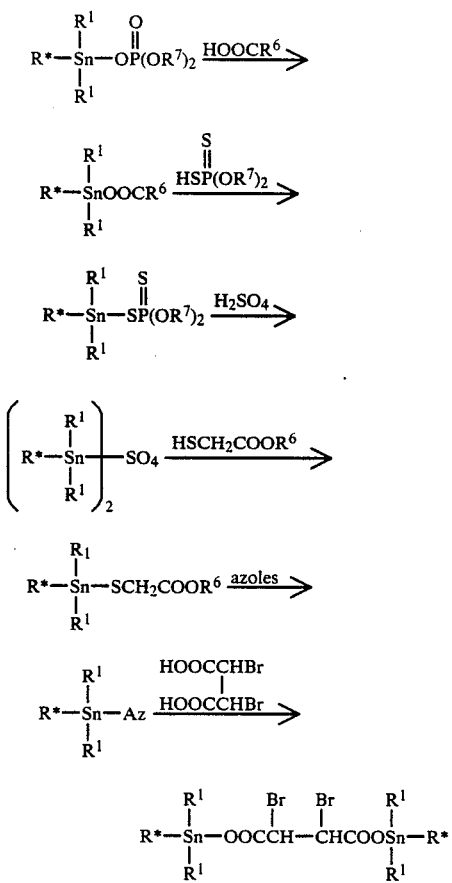

In the above schemes, R*, $R^1$, $R^6$, $R^7$, $R^8$, $R^9$, $R^{10}$ and Hal are as defined previously, Az is 1,3-imidazol-1-yl or 1,2,4-triazol-1-yl. Desirable conditions for the reactions shown in the above schemes are known in the art, and disclosed, for example, by R. Inhan, Chemical Reviews, 459–539, 1960(October).

The compounds of formula (I) of the present invention exhibit an excellent pesticidal activity against phytophagous pests of various orders, such as Acarina, Lepidoptera, Hemiptera, Coleoptera, Orthoptera and Diptera. In particular, the compounds (I) exhibit an excellent inhibiting activity against a wide variety of acarina such as citrus red mite (*Panonychus citri*), European red mite (*Panonychus ulmi*), hawthorn spider mite (*Tetranychus viennensis*), Kanzawa spider mite (*Tetranychus kanzawai*), citrus flat mite (*Brevipalpus lewisi*), privet mite (*Brevipalpus obovatus*) and pink citrus rust mite (*Aculops pelekassi*). Moreover, the compounds (I) exert no harm, or only minor harm which is easily repaired, on crops and garden plants.

A certain class of spider mites, for example the kanzawa spider mite, shows resistance to known acaricides, cyhezatin (Plictran®, Dow Chemical Co., see U.S. Pat. No. 3,264,177), and fenbutatin oxide (Osadan®, Shell Oil Co., see U.S. Pat. No. 3,657,451). The compounds (I) of the invention, as stated before, show an excellent inhibiting activity even to the mites having resistance against such known acaricides.

Therefore, the present invention also provides a pesticidal composition which comprises as an active ingredient a compound of formula (I) together with a suitable carrier and/or adjuvant.

The pesticidal composition of the invention can be in any desirable form, such as wettable powders, emulsifiable concentrates, dusts or flowables, and prepared by mixing a compound (I) with one or more of non-phytotoxic carriers or adjuvants in accordance with conventional methods in the art. Such carriers and adjuvants include various liquid substances such as organic solvents and water, surfactants, granular or fine solid substances, and the like.

Wettable powders may be obtained by mixing a compound (I) with a solid carrier, such as clay, talc, white carbon, diatomaceous earth or bentonite, an ionic or nonionic emulsifier or dispersing agent, such as higher alkoxysulfonate, polyoxyehtylenesorbitan, alkylphenoxypolyethoxyethanol or lignosulfonate, and if required, wetting agents, protective colloid and the like. Emulsifiable concentrates may be obtained by dissolving a compound (I) in a suitable organic solvent and then adding thereto an appropriate surfactant. The emulsifiable concentrates can exist as water-in-oil concentrates or as oil-in-water concentrates having a high concentration comparable to a condensed mayonnaise.

The pesticidal compositions of the invention may be employed alone or after mixing with other acaricidal, insecticidal, or fungicidal compositions, plant growth regulator, fertilizer or the like.

The content of the compound (I) in the pesticidal composition in the form of wettable powder or emulsifiable concentrate is generally from 7 to 70 percent by weight, preferably from 20 to 50 percent by weight. The amount of the composition to be applied to loci of pests will vary depending on a number of factors, such as a method, season or locus of application, species of pests and crops, and the like. However, the composition is usually applied at the application rate of 200 to 600 liter per 10 are, after diluted to 500 to 10,000 fold, preferably 1,000 to 5,000 fold.

Dust compositions usually contain from 0.5 to 10 percent, preferably from 2 to 5 percent by weight of the compound (I), and are applied at application rate of from 3 to 5 kg per 10 are. Fine dust compositions contain the compounds (I) in the range of from 0.5 to 10 percent, preferably 1 to 5 percent by weight, and are applied at the rate in the range of from 1.5 to 5 kg per 10 are.

The following detailed Examples, Formulations and Experiments are presented by way of illustration of certain specific embodiments of the invention.

EXAMPLE 1

Dineophyl-metatrifluoromethylphenyltin fluoride (compound 1)

(1) Dineophyl-di(metatrifluoromethylphenyl)tin

A 1,000 ml four-necked flask equipped with a stirrer, a thermometer, a dropping funnel and a condenser was charged with magnesium (12.5 g, 0.51 mol) and flushed with nitrogen. Each 3 ml of a mixture of metatrifluoromethylphenyl bromide (113.4 g, 0.504 mol) and tetrahydrofuran (220 g) was portionwise added from the dropping funnel. The reaction occurred with fuming when the mixture was heated to 60°–70° C. While the temperature of the solution was maintained at 60° C., the solution of metatrifluoromethylphenyl bromide dissolved in tetrahydrofuran was added dropwise over about 2 hours.

After completion of the addition, the mixture was refluxed for 5 hours and then cooled to room temperature. Next, a solution of dineophyltin dichloride (85.6 g, 0.188 mol) dissolved in tetrahydrofuran (200 g) was dropwise added from a dropping funnel over 30 minutes, while maintaining the temperature at 10° to 20° C. After the addition, the mixture was kept at the reflux temperature for 7 hours. The mixture was then cooled to room temperature and hydrolyzed by the addition of a saturated aqueous ammonium chloride solution. The organic layer was separated, washed with water, filtered and concentrated under reduced pressure to yield a brown viscous liquid. To this substance was added n-hexane (300 g) and activated clay (50 g) for decolorization. The mixture was filtered and concentrated under reduced pressure to obtain 118 g of dineophyl-di(metatrifluoromethylphenyl)tin as a colorless, clear and viscous liquid. Analysis by gas chromatography of the viscous liquid showed 95% purity. Tin content was 17.2% (theoretical: 17.6%).

(2) Dineophyl-metatrifluoromethylphenyltin fluoride

A 500 ml four-necked flask with a stirrer, a thermometer, a dropping funnel and a condenser was charged with dineophyl-dl(metatrifluoromethylphenyl)tin (80 g, 0.118 mol) obtained in Example 1-(1) and chloroform (200 g). A mixture of bromine (19 g, 0.216 gram atom) and chloroform (100 ml) was dropwise added from the dropping funnel over about 2.5 hours with stirring, while maintaining the temperature of the reaction mixture at −5° to 0° C. After completion of the addition, the mixture was allowed to warm to room temperature, filtered and concentrated under reduced pressure to give 72.2 g of dineophyl-metatrifluoromethylphenyltin bromide as a viscous liquid. The purity of the liquid was 93% based on a gas chromatography analysis. Crude dineophyl-metatrifluoromethylphenyltin bromide (72.2 g) thus prepared, benzen (120 g), potassium fluoride (14 g) and water (56 g) were charged into a 500 ml three-necked flask, and the mixture was refluxed for 2 hours. After completion of the reaction, the aqueous layer was separated off and the organic layer was washed with water, filtered and concentrated under reduced pressure. The resulting residue was crystallizred from n-hexane at the temperature of −20° C. to obtain 33.8 g of dineophyl-metatrifluoromethylphenyltin bromide. This substance was a liquid at room temperature and has a refractive index of $n^{30}=1.5555$. Tin content was 21.1% (theoretical: 21.6%).

EXAMPLE 2

Bis(dineophyl-metatrifluoromethylphenyltin)oxide (Compound 3)

Dineophyl-metatrifluoromethylphenyltin fluoride (13 g, 23.7 mmol) obtained in Example 1 was dissolved in benzene (60 g). To the resultant solution was added a 20% aqueous sodium hydroxide solution (7.2 g), and the mixture was allowed to react for one hour at a temperature between 75° C. and 80° C. After completion of the reaction, the aqueous layer was removed and the organic layer was washed with water and filtered. The benzene was distilled of from the organic layer under reduced pressure to yield 11.8 g of bis(dineophyl-metatrifluoromethylphenyltin)oxide as a pale-yellow viscous liquid. Refractive index: $n^{30}=1.5651$; Tin content: 21.9% (theoretical: 22.1%).

EXAMPLE 3

Dineophyl-metatrifluoromethylphenyltin acetate (compound 5)

Bis(dineophyl-metatrifluoromethylphenyltin)oxide (6 g, 5.57 mmol) prepared in Example 2 was dissolved in n-hexane (30 g). To this solution was added glacial acetic acid (0.67 g, 11.16 mmol), and the mixture was heated at temperature of 70° to 75° C. for one hour to effect an azeotropic dehydration. After completion of the reaction, the mixture was filtered, and n-hexane was distilled off from the filtrate to obtain 6.4 g of dineophyl-metatrifluoromethylphenyltin acetate as a pale-yellow viscous liquid. Refractive indes: $n^{30}=1.5465$. Tin content: 20.1% (theoretical: 20.1%).

EXAMPLE 4

Dineophyl-metatrifluoromethylphenyltindimethyldithiocarbamate (compound 6)

Dineophyl-metatrifluoromethylphenyltin fluoride (10 g, 18.2 mmol) prepared in Example 1 was dissolved in benzene (50 g), and the resulting solution was added with a solution of sodium dimethyldithiocarbamate dihydrate (3.9 g, 21.8 mmol) dissolved in water (15.6 g). The mixture was heated at a temperature of from 75° to 80° C. for one hour. The aqueous layer was removed and the organic layer was washed with water and filtered. The filtrate was distilled to remove the benzene under reduced pressure and the resultant residue was recrystallized from petroleum ether to give 11.4 g of dineophyl-metatrifluoromethylphenyltindimethyldithiocarbamate as a white solid.

Mp: 96°–97° C. Tin content: 18.1% (theoretical: 18.2%).

EXAMPLE 5

Dineophyl-orthotrifluoromethylphenyltin chloride (compound 25)

Dineophyl-diorthotrifluoromethylphenyltin (113 g), a pale-yellow viscous liquid, was prepared in accordance with the teaching of Example 1 except that orthotrifluoromethylphenyl bromide (113.4 g, 0.502 mol), rather than metatrifluoromethylphenyl bromide, was used. Analysis of the resulting liquid by gas chromatography showed 96.3% purity. Tin content was 17.3%(theoretical: 17.6%).

Dineophyl-diorthotrifluoromethylphenyltin (80 g, 0.108 mol) obtained above was dissolved in chloroform (200 g). Chlorine gas (7.6 g, 0.216 gram atom) was then introduced into the resultant solution while keeping the temperature of the solution at between 0° C. and 5° C. The reaction mixture was then concentrated under reduced pressure and the resulting residue was recrystallized from methanol to yield 61.1 g of dineophyl-orthotrifluoromethylphenyltin chloride as a white solid. Analysis by gas chromatography of the solid indicated 97.3% purity.

Mp: 49°–50° C. Tin content: 21.0%(theoretical: 21.0%).

EXAMPLE 6

Bis(dineophyl-orthotrifluoromethylphenyltin)oxide (compound 16)

Dineophyl-orthotrifluoromethylphenyltin chloride (13.4 g, 23.7 mmol) obtained in Example 5 was hydrolyzed in accordance with the procedure described in Example 2 and the resultant product was recrystallized from n-hexane to give 12.1 g of bis(dineophyl-orthotrifluoromethylphenyltin)oxide.

Mp: 42°–44° C. Tin content: 21.8%(theoretical: 22.1%).

EXAMPLE 7

Dineophyl(orthotrifluoromethylphenyl) (1,2,4-triazole-1-yl)tin (compound 7)

Bis(dineophyl-orthotrifluoromethylphenyltin)oxide (6 g, 5.57 mmol) prepared in Example 6 and 1,2,4-triazole (0.77 g, 11.1 mmol) were dissolved in toluene (30 g), and the mixture was heated at 110°–112° C. for one hour to perform an azeotropic dehydration. The reaction mixture was filtered and distilled to remove the benzene, which gave 6.5 g of (dineophyl) (orthotrifluoromethylphenyl) (1,2,4-triazol-1-yl)tin as a pale-yellow viscous liquid.

Refractive index: $n^{30}=1.5690$. Tin content: 20.7% (theoretical: 19.8%).

EXAMPLE 8

Bis(dineophyl-orthotrifluoromethylphenyltin)sulfate (compound 55)

Bis(dineophyl-orthotrifluoromethylphenyltin)oxide (2.7 g, 2.51 mmol) prepared in Example 6 was dissolved in benzene (30 ml). To the resultant solution was added a 50% aqueous sulfuric acid solution (5 ml) and the mixture was stirred at room temperature for 15 minutes. The aqueous layer was separated and removed, and the organic layer washed with water, filtered and concentrated under reduced pressure to give 2.8 g of bis(-dineophyl-orthotrifluoromethylphenyltin)sulfate as a pale-yellow viscous liquid.

Refractive index: $n^{30}=1.5700$. Tin content: 21.0% (theoretical: 20.5%).

EXAMPLE 9

Dineophyl-p-fluorophenyltin fluoride (compound 9)

Dineophyl-diparafluorophenyltin (100.9 g) was obtained as a colorless viscous liquid, in accordance with the teaching of Example 1-(1) except that para-fluorophenyl bromide (89.3 g, 0.51 mol), rather than metatrifluoromethylphenyl bromide, was employed.

Gas chromatography analysis of this liquid showed 96.9% purity of the desired compound. Tin content was 20.6% (theoretical: 20.6%).

Dineophyl-di(parafluorophenyl)tin (62.1 g, 0.108 mol) prepared above was dissolved in chloroform (200 g). While the resulting solution was maintained at $-15°$ to $-20°$ C., chlorine gas (7.6 g, 0.216 gram atom) was introduced. The mixture was then concentrated under reduced pressure to give 56 g of dineophyl-parafluorophenyltin chloride as a pale-yellow liquid. Gas chromatography analysis indicated 87.5% purity of the desired product.

A mixture consisting of the crude dineophyl-parafluorophenyltin chloride (50 g) and potassium fluoride (5.8 g, 0.1 mol) was heated for 2 hours in the presence of benzene (120 g) and water (23 g). The aqueous layer of the reaction mixture was removed, and the organic layer was washed with water, filtered and concentrated under reduced pressure. The residue thus obtained was crystallized from petroleum ether to give 38.5 g of dineophyl-parafluorophenyltin fluoride as a white solid.

Mp: 59°–62° C. Tin content: 23.2% (theoretical: 23.8%).

EXAMPLE 10

Bis(dineophyl-parafluorophenyltin)sulfide (compound 58)

Dineophyl-parafluorophenyltin fluoride (6 g, 12 mmol) obtained above was dissolved in benzene (30 ml). To this solution was added potassium sulfide (1 g, 17.7 mmol) dissolved in water (4 g) and the mixture was refluxed for 2 hours.

After the aqueous layer was separated and removed from the mixture, the organic layer washed with water and filtered. Evaporation of the benzene under reduced pressure yielded 6.4 g of bis(dineophyl-parafluorophenyltin)sulfide as a pale-yellow viscous liquid.

Refractive index: $n^{30}=1.6155$. Tin content: 23.1% (theoretical: 23.9%).

EXAMPLE 11

Bis(dineophyl-parafluorophenyltin)oxide (compound 17)

Using dineophyl-parafluorophenyltin fluoride (15 g, 30 mmol) prepared in Example 9 and a 20% aqueous sodium hydroxide solution (9 g), bis(dineophyl-parafluorophenyltin)oxide was prepared in accordance with the procedure as described in Example 2, as a white solid.

Mp: 84°–86° C. Tin content: 24.5% (theoretical: 24.3%).

EXAMPLE 12

Dineophyl(parafluorophenyl) (1,3-imidazol-1-yl)tin (compound 54)

Bis(dineophyl-parafluorophenyltin)oxide (6 g, 6.14 mmol) prepared in Example 11 and 1,3-imidazole (0.83 g, 12.3 mmol) were dissolved in toluene (30 g) and the mixture was heated at 110°–112° C. for one hour to effect an azeotropic dehydration. Filtration of the reaction mixture and evaporation of the benzene gave a solid residue, which was crystallized from n-hexane to yield 5.1 g of dineophyl(parafluorophenyl) (1,3-imidazol-1-yl)tin.

Mp: 123°–127° C. Tin content: 21.2% (theoretical: 21.7%).

EXAMPLE 13

Dicyclohexyl-parafluorophenyltin fluoride (compound 14)

Dicyclohexyl-diparafluorophenyltin (85.2g) was prepared in accordance with the procedure as described in Example 1(1) except that parafluorophenyl bromide (89.3 g, 0.51 mol) and dicyclohexyltin dichloride (76.9 g, 0.216 mol), rather than metatrifluoromethylphenyl bromide and dineophyltin dichloride, were employed. Gas chromatography of the recrystallized product from isopropanol showed 98.6% purity.

Mp: 88°–90° C. Tin content: 25.1% (theoretical: 25.0%).

In accordance with the procedure as described in Example 1(2), the above product (20 g, 0.042 mol) was first reacted with bromine to produce crude dicyclohexyl-parafluorophenyltin bromide, which was then treated with sodium fluoride to yield 11.7 g of dicyclohexyl-parafluorophenyltin fluoride as a white solid.

Mp: 234°–240° C. (dec.). Tin content: 29.9% (theoretical: 29.7%).

EXAMPLE 14

Dineophyl-orthotrifluoromethylphenyltin isocyanate (compound 60)

Dineophyl-orthotrifluoromethylphenyltin chloride (6 g, 10.6 mmol) prepared in Example 5, sodium cyanate (1.1 g, 15.9 mmol) and acetone (40 g) were charged into a flask and the mixture was refluxed for 3 hours. The mixture was then added with benzene (50 g) and water (30 g). The aqueous layer was removed, and the organic layer was washed with water and filtered.

Evaporation of the benzene under reduced pressure gave 5.6 g of dineophyl-orthotrifluoromethylphenyltin isocyanate as a colorless viscous liquid.

Refractive index: $n^{30} = 1.5609$. Tin content: 21.0% (theoretical: 20.7%).

EXAMPLE 15

Dineophyl-orthotrifluoromethylphenyltin isothiocyanate (compound 59)

Dineophyl-orthotrifluoromethylphenyltin chloride (6 g, 10.6 mmol) prepared in Example 5, potassium thiocyanate (1.5 g, 15.9 mmol), benzene (40 g) and water (10 g) were charged into a flask and the mixture was refluxed for 2 hours. The aqueous layer was removed and the organic layer was washed with water and filtered. Evaporation of the benzene under reduced pressure gave 6.0 g of dineophyl-orthotrifluoromethylphenyltin isothiocyanate as a colorless viscous liquid.

Refractive index: $n^{30} = 1.5787$. Tin content: 20.5% (theoretical: 20.2%).

EXAMPLE 16

Dineophyl-orthotrifluoromethylphenyltin methylsulfide (compound 67)

Dineophyl-orthotrifluoromethylphenyltin chloride (6 g, 10.6 mmol) prepared in Example 5, a 15% aqueous sodium methylsulfide solution (7.4 g, 15.9 mmol) and benzene (40 g) were charged into a flask and the mixture was refluxed for 2 hours. The aqueous layer was removed and the organic layer was washed with water and filtered. Evaporation of the benzene under reduced pressure yielded 4.6 g of dineophyl-orthotrifluoromethylphenyltin methylsulfide as a colorless viscous liquid.

Refractive index: $n^{30} = 1.5804$. Tin content: 20.9% (theoretical: 20.6%).

EXAMPLE 17

Dineophyl-orthotrifluoromethylphenyltin phenoxide (compound 68)

Bis(dineophyl-orthotrifluoromethylphenyltin)oxide (6 g, 5.6 mmol) prepared in Example 6, phenol (1.0 g, 11.2 mmol) and toluene (40 g) were charged into a flask and the mixture was allowed to react substantially in accordance with the procedure described in Example 7. Evaporation of the toluene followed by recrystallization of the resulting residue from petroleum ether yielded 4.4 g of dineophyl-orthotrifluoromethylphenyltin phenoxide as a white solid.

Mp: 69°–71° C. Tin content: 19.1% (theoretical: 19.0%).

EXAMPLE 18

Dineophyl-orthotrifluoromethylphenyltin phenylsulfide (compound 69)

A mixture of bis(dineophyl-orthotrifluoromethylphenyltin)oxide (6.0 g, 5.6 mmol) prepared in Example 6, thiophenol (1.2 g, 11.2 mmol) and toluene (40 g) was treated with the procedure described in Example 7. The product was recrystallized from n-hexane to obtain 5.2 g of dineophyl-orthotrifluoromethylphenyltin phenylsulfide as a white solid.

Mp: 81°–82° C. Tin content: 18.7% (theoretical: 18.6%).

EXAMPLE 19

S-Dineophyl-orthotrifluoromethylphenyltin) O,O-diethyldithiophosphate (compound 71)

In substantial accordance with the procedure described in Example 7, a mixture of bis(dineophyl-orthotrifluoromethylphenyltin)oxide (6.8 g, 6.4 mmol) prepared in Example 6, O,O-diethyldithiophosphate (2.2 g, 12.8 mmol) and toluene (40 g) was reacted to provide 8.0 g of S-(dineophyl-orthotrifluoromethylphenyltin) O,O-diethyldithiophosphate as a colorless viscous liquid.

Refractive index: $n^{30} = 1.5759$.

EXAMPLE 20

Dineophyl (4-chloro-3-trifluoromethylphenyl)tin bromide (compound 74)

Dineophyl-di(4-chloro-3-trifluoromethylphenyl)tin (125.8), a pale-yellow viscous liquid, was prepared in substantial accordance with the procedure described in Example 1-(1) except that 4-chloro-3-trifluoromethylphenyl bromide (131.0 g, 0.504 mol), rather than meta-trifluoromethylphenyl bromide, was employed. Gas chromatography analysis of this liquid showed 98.5% purity. Tin content was 15.6% (theoretical: 15.9%).

Following the procedure described in Example 1-(2), dineophyl-di(4-chloro-3-trifluoromethylphenyl)tin (87.8 g, 0.118 mol) obtained above was then reacted with bromine to obtain a pale yellow solid (79.2 g). This solid was recrystallized from methanol (200 g) to give 65.7 g of dineophyl-4-chloro-3-trifluoromethylphenyltin bromide as a white solid. Gas chromatography analysis of this solid showed 99.0% purity. Mp: 72°–74° C. Tin content: 18.3% (theoretical: 18.4%).

EXAMPLE 21

Dineophyl-2,4-difluorophenyltin fluoride (compound 79)

Dineophyl-di(2,4-difluorophenyl)tin (107.9 g), a colorless viscous liquid, was prepared according to the procedure described in Example 1-(1) except that 2,4-difluorophenyl bromide (98.4 g, 0.51 mol), rather than metatrifluoromethylphenyl bromide, was used. Gas chromatography analysis of this liquid showed 95.5% purity. Tin content was 19.0% (theoretical: 19.4%).

Next, following the procedure described in Example 1(2), the above product (72.1 g, 0.118 mol) was reacted with bromine to obtain crude dineophyl-2,4-difluorophenyltin bromide, which was then treated with sodium fluoride. Recrystallization of the resultant product from n-hexane gave 30.6 g of dineophyl-2,4-difluorophenyltin fluoride as a white solid.

Mp: 60°-65° C. Tin content: 22.6% (theoretical: 22.9%).

EXAMPLE 22

Dineophyl-2,4,5-trifluorophenyltin chloride (compound 92)

Dineophyl-di(2,4,5-trifluorophenyl)tin (113.1 g), a pale-yellow viscous liquid, was prepared in substantial accordance with the procedure described in Example 1(1) except that 2,4,5-trifluorophenyl bromide (105.9 g, 0.502 mol), rather than metatrifluoromethylphenyl bromide, was employed. Gas chromatography analysis of this liquid showed 96.0% purity. Tin content was 17.8% (theoretical: 18.3%).

The above product (76.4 g, 0.118 mol) was then reacted with chlorine and the reaction mixture was worked up in substantial accordance with the procedure described in Example 5. Recrystallization of the product from n-hexane gave 39.3 g of dineophyl-2,4,5-trifluorophenyltin chloride as a white solid. Gas chromatography analysis of this solid showed 99.9% purity.

Mp: 65°-67° C. Tin content: 21.7% (theoretical: 21.5%).

EXAMPLE 23

Dineophyl-parachlorophenyltin fluoride (compound 108)

Dineophyl-di(parachlorophenyl)tin (107.5 g), a colorless viscous liquid, was prepared in substantial accordance with the procedure described in Example 1 except that metachlorophenyl bromide (97.4 g, 0.51 mol), rather than metatrifluoromethylphenyl bromide, was employed. Gas chromatography analysis of this liquid indicated 97.5% purity. Tin content was 19.1% (theoretical: 19.5%).

In substantial accordance with the procedure described in Example 1(2), the above product (71.8 g, 0.118 mol) was reacted with bromine to obtain crude dineophyl-metachlorophenyltin bromide, which was then reacted with sodium fluoride. The resulting product was recrystallized from n-hexane to provide 32.7 g of dineophyl-metachlorophenyltin fluoride as a white solid.

Mp: 104°-105° C. Tin content: 23.0% (theoretical: 23.0%).

EXAMPLE 24

Dineophyl-phenyltin fluoride (compound 144)

Dineophyl-diphenyltin (108.9 g), a colorless viscous liquid, was prepared in substantial accordance with the procedure described in Example 1-(1) except that phenyl bromide (78.8 g, 0.502 mol), rather than metatrifluoromethylphenyl bromide, was employed. Gas chromatography analysis of this liquid showed 97.8% purity. Tin content was 21.7% (theoretical: 22.0%).

Dineophyl-phenyltin fluoride (39.6 g), a white solid, was prepared using the above product (80 g, 0.128 mol) as described in Example 1(2).

Mp: 37°-40° C. Tin content: 24.9% (theoretical: 24.7%).

EXAMPLE 25

Dineophyl-orthomethoxyphenyltin chloride (compound 133)

Dineophyl-di(orthomethoxyphenyl)tin (105.9 g), a colorless viscous liquid, was prepared in substantial accordance with the procedure described in Example 1(1) except that orthoanisyl bromide (93.8 g, 0.502 mol), rather than metatrifluoromethylphenyl bromide, was employed. Gas chromatography analysis of this liquid showed 96.5% purity. Tin content was 19.5% (theoretical: 19%).

Dineophyl-orthomethoxyphenyltin chloride (30.1 g), a white solid, was prepared using the above product (70.7 g, 0.118 mol) and chlorine in the manner as described in Example 5. Gas chromatography analysis of this solid showed 99.5% purity.

Mp: 69°-72° C. Tin content: 22.7% (theoretical: 22.5%).

EXAMPLE 26

Dineophyl-3-thienyltin fluoride (compound 215)

(1) Dineophyl-di(3-thienyl)tin

A 1,000 ml four necked flask equipped with a stirrer, a thermometer, a dropping funnel and a condenser was charged with 3-thienyl bromide (75 g, 0.0461 mol) and absolute ether (200 g). n-Butyl lithium (185.3 g) (15% solution in n-hexane) was added in dropwise fashion from the dropping funnel while maintaining the temperature of the reaction mixture at below −50° C. After completion of the addition, the reaction mixture was stirred for about 10 minutes at below −50° C. and then added with a solution of dineophyltin dichloride (73.5 g, 0.161 mol) dissolved in tetrahydrofuran (140 g) through the dropping funnel at −50° to −60° C. over about 30 minutes. After completion of the addition, the mixture was stirred for about 2 hours at that temperature, allowed to warm to room temperature and stirred for about additional one hour. The reaction mixture was then hydrolyzed by the addition of water (120 ml). The organic layer was separated, added with hexane (200 g), washed with water, filtered and concentrated under reduced pressure to yield a brown viscous liquid. To this liquid were added n-hexane (300 g) and activated clay (50 g) for dicolorization. The mixture was filtered and concentrated under reduced pressure to obtain 81.7 g of dineophyl-di(3-thienyl)tin as a colorless, transparent and viscous liquid. Gas chromatography analysis of this liquid showed 95.0% purity. Tin content was 21.0% (theoretical: 21.6%).

(2) Dineophyl-3-thienyltin fluoride

In substantial accordance with the procedure described in Example 1(2), dineophyl-di(3-thienyl)tin (80 g, 0.145 mol) obtained above was reacted with bromine to give crude dineophyl-3-thienyltin bromide, which was then reacted with sodium fluoride. The resulting product was recrystallized from n-hexane to provide 21.5 g of dineophyl-3-thienyltin fluoride as a white solid.

Mp: 85°-90° C. Tin content: 24.7% (theoretical: 24.4%).

EXAMPLE 27

Dicyclohexyl-paratrifluoromethylphenyltin chloride (compound 164)

Crude dicyclohexyl-di(paratrifluoromethylphenyl)-tin (101.7 g), a white solid, was prepared in accordance with the procedure described in Example 1(1) except that paratrifluoromethylphenyl bromide (113.4 g, 0.504 mol) and dicyclohexyltin dichloride (66.9 g, 0.188 mol), rather than metatrifluoromethylphenyl bromide and dineophyltin dichloride, were employed. Gas chromatography analysis of this solid indicated 93.3% purity.

In substantial accordance with the procedure described in Example 5, the above product (60 g, 0.105 mol) was then reacted with chlorine and the resulting mixture was worked up to yield 31.5 g of dicyclohexyl-paratrifluoromethylphenyltin chloride as a white solid. gas chromatography analysis of this solid indicated 99.0% purity.

Mp: 74°–75° C. Tin content: 25.8% (theoretical: 25.5%).

EXAMPLE 28

Bis(dicyclohexyl-paratrifluoromethylphenyltin)oxide (compound 165)

Dicyclohexyl-paratrifluoromethylphenyltin chloride (15.0 g, 32.2 mmol) prepared in Example 27 was treated in the manner as described in Example 6 to provide 11.3 g of bis(dicyclohexyl-paratrifluoromethylphenyltin)oxide as a white solid.

Mp: 86°–89° C. Tin content: 26.8% (theoretical: 27.1%).

Dicyclohexyl-paratrifluoromethylphenyltin-n-butylthioglycolate (compound 167)

Bis-(dicyclohexyl-paratrifluoromethylphenyltin)oxide (6 g, 16.8 mmol) prepared in Example 28 and n-butyl thioglycolate (2.0 g, 13.6 mmol) were dissolved in toluene (30 g) and the mixture was heated at 110°–112° C. for one hour to effect an azeotropic dehydration. Evaporation of the toluene under reduced pressure gave 7.8 g of pale-yellow liquid.

Refractive index: $n^{30}$=1.5337. Tin content: 20.4% (theoretical: 20.6%).

EXAMPLE 30

Dicyclohexyl-3,4-dichlorophenyltin fluoride (compound 190)

Dicyclohexyl-di(3,4-dichlorophenyl)tin (191.9 g), a colorless viscous liquid, was prepared in substantial accordance with the procedure described in Example 1(1) except that 3,4-dichlorophenyl bromide (113.8 g, 0.504 mol) and dicyclohexyltin dichloride (66.9 g, 0.188 mol), rather than metatrifluoromethylphenyl bromide and dineophyltin dichloride, were employed. Gas chromatography analysis of this liquid showed 95.9% purity. Tin content was 20.2% (theoretical: 20.6%).

Dicyclohexyl-di(3,4-dichlorophenyl)tin (86.5 g, 0.150 mol) prepared above was allowed to react and the resulting mixture was worked up, as described in Example 1-(2), to obtain 35.5 g of dicyclohexyl-3,4-dichlorophenyltin fluoride as a white solid.

Mp: 193° C. Tin content: 26.0% (theoretical: 26.4%).

EXAMPLE 31

Dicyclohexyl-paratolyltin chloride (compound 197)

Dicyclohexyl-di(paratolyl)tin (82.5 g), a pale-yellow viscous liquid, was prepared in substantial accordance with the procedure described in Example 1(1) except that paratolyl bromide (86.2 g, 0.504 mol) and dicyclohexyltin dichloride (66.9 g, 0.188 mol), rather than metatrifluoromethylphenyl bromide and dineophyltin dichloride, were employed. gas chromatography analysis of this liquid showed 94.5% purity. Tin content was 24.7% (theoretical: 25.4%).

The above product (70 g, 0.150 mol) was then allowed to react with chlorine and the resulting mixture was worked up, as described in Example 5, to obtain 34.5 g of dicyclohexyl-paratolyltin chloride as a colorless viscous liquid. Gas chromatography analysis of this liquid showed 98.4% purity.

Refractive index: $n^+$=1.5705. Tin content: 28.6% (theoretical: 28.8%).

EXAMPLE 32

Dicyclohexyl-trimethylsilylmethyltin chloride (compound 232)

(1) Dicyclohexyl-phenyltin chloride

Dicyclohexyl-di(phenyl)tin (155.2 g), a white solid, was prepared in substantial accordance with the procedure described in Example 1(1) except that phenyl bromide (156.2 g, 1.008 mol) and dicyclohexyltin dichloride (133.8 g, 0.376 mol), rather than metatrifluoromethylphenyl bromide and dineophyltin dichloride, were employed. Gas chromatography analysis of this solid showed 94.9% purity.

The above product (150.8 g, 0.343 mol) was then allowed to react with chlorine and the resultant mixture was worked up as described in Example 5. Recrystallization of the product from n-hexane gave 86.0 g of dicyclohexyl-phenyltin chloride as a white solid. Gas chromatography analysis of this solid showed 98.8% purity.

MP: 50°–52° C. Tin content: 30.2% (theoretical: 29.9%)

(2) Dicyclohexyl-trimethylsilylmethyltin chloride

Dicyclohexyl-phenyl-trimethylsilylmethyltin (79.4 g), a colorless viscous liquid, as prepared as described in Example 1(1). Using dicyclohexyl-phenyltin chloride (74.7 g, 0.188 mol) obtained above and trimethylsilylmethyl cloride (30.8 g, 0.251 mol) instead of dineophyltin dichloride and metatrifluoromethylphenyl bromide respectively. In this example, 6.1 g (0.251 mol) of magnesium and 110 g of tetrahydrofuran were employed. Gas chromatography analysis of this liquid showed 97.5% purity.

In the manner as taught in Example 5, the above product (48.5 g, 0.108 mol) was reacted with chlorine, and the resultant mixture was concentrated. The residue was recrystallized from n-hexane to yield 35.2 g of dineophyl-trimethylsilylmethyltin chloride as a white solid. Gas chromatography analysis of this solid showed 99.0% purity.

Mp: 74° C.

EXAMPLE 33

Bis(dicyclohexyl-trimethylsilylmethyltin)oxide (compound 233)

Dicyclohexyl-trimethylsilylmethyltin chloride (25.3 g, 0.062 mol) prepared in Example 32 was allowed to react and the resultant mixture was worked up, as described in Example 2, to provide 21.2 g of bis(dicyclohexyl-trimethylsilylmethyltin)oxide as a white solid. Mp: 151°–153° C.

EXAMPLE 34 o-(Dicyclohexyl-trimethylsilylmethyltin) o,o-dibutylphosphate (compound 237)

Bis(dicyclohexyl-trimethylsilylmethyltin)oxide (6.8 g, 8.9 mmol), o,o-dibutylphosphate (3.7 g, 17.8 mmol) and toluene (40 g) were allowed to react as described in Example 7. Evaporation of the toluene from the mixture and recrystallization of the residue from methanol-/acetonitrile gave 8.3 g of o-(dicyclohexyl-trimethyl-silylmethyltin) o,o-dibutylphosphate as a white solid. Mp: 130°–132° C.

In substantial accordance with the procedures as taught in the above examples, a variety of organotin compounds (I) of the invention were prepared. Physicochemical properties of the compounds are listed in Table 1.

In Table 1, the following abbreviations were employed:
Me: methyl
Et: ethyl
Bu: butyl
Oct: octyl
Phe: phenyl
Ac: acetyl Tin content in parenthesis represents theoretical amount.

TABLE 1-1

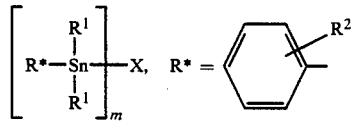

| Compound No. | R² | R¹ | m | X | Appearance | m.p. or b.p. | $n^{30}$ | Tin content (%) | GLC purity (%) |
|---|---|---|---|---|---|---|---|---|---|
| 1 | m-CF₃ | Neophyl | 1 | F | Viscous liquid | | 1.5555 | 21.1 (21.6) | |
| 2 | p-F | n-Butyl | 1 | F | White solid | 205–210° C. | | 34.2 (34.4) | |
| 3 | m-CF₃ | Neophyl | 2 | —O— | Viscous liquid | | 1.5651 | 21.9 (22.1) | |
| 4 | m-CF₃ | Neophyl | 1 | Cl | Colorless liquid | | 1.5591 | 21.2 (21.0) | 99.3 |
| 5 | m-CF₃ | Neophyl | 1 | —OCOMe | Viscous liquid | | 1.5465 | 20.1 (20.1) | |
| 6 | m-CF₃ | Neophyl | 1 | —SSCN(Me)₂ | White solid | 96–97° C. | | 18.1 (18.2) | |
| 7 | o-CF₃ | Neophyl | 1 | Triazolyl | Viscous liquid | | 1.5690 | 20.7 (19.8) | |
| 8 | o-CF₃ | Neophyl | 1 | F | White solid | 38–40° C. | | 21.0 (21.6) | |
| 9 | p-F | Neophyl | 1 | F | White solid | 59–62° C. | | 23.2 (23.8) | |
| 10 | m-F | Neophyl | 1 | F | White solid | 35–38° C. | | 23.3 (23.8) (mg) | |
| 11 | o-CF₃ | n-Butyl | 1 | F | White solid | 105–111° C. (decomp.) | | 29.2 (29.9) | |
| 12 | m-CF₃ | n-Butyl | 1 | F | White solid | 142° C. (decomp.) | | 29.2 (29.9) | |
| 13 | p-F | n-Octyl | 1 | F | White solid | 57–60° C. | | 26.0 (25.8) | |
| 14 | p-F | Cyclohexyl | 1 | F | While solid | 235–240° C. (decomp.) | | 29.9 (29.7) | |
| 15 | m-CF₃ | Cyclohexyl | 1 | F | While solid | 280° C. (decomp.) | | 26.8 (26.4) | |
| 16 | o-CF₃ | Neophyl | 2 | —O— | White solid | 42–44° C. | | 21.8 (22.1) | |
| 17 | p-F | Neophyl | 2 | —O— | White solid | 84–86° C. | | 24.5 (24.3) | |
| 18 | m-F | Neophyl | 2 | —O— | White solid | 37–39° C. | | 24.6 (24.3) | |
| 19 | o-CF₃ | n-Butyl | 2 | —O— | Colorless liquid | | 1.5031 | 31.3 (32.2) | |
| 20 | m-CF₃ | n-Butyl | 2 | —O— | Colorless liquid | | 1.4939 | 30.8 (30.7) | |
| 21 | p-F | n-Butyl | 2 | —O— | Colorless liquid | | 1.5285 | 35.3 (35.3) | |
| 22 | p-F | n-Octyl | 2 | —O— | Colorless liquid | | 1.5084 | 26.5 (26.5) | |
| 23 | p-F | Cyclohexyl | 2 | —O— | White solid | 69–72° C. | | 30.4 (30.6) | |
| 24 | m-CF₃ | n-Butyl | 1 | Br | Colorless liquid | 170–172° C./ 7 mmHg | 1.5109 | 25.5 (25.9) | 96.3 |
| 25 | o-CF₃ | Neophyl | 1 | Cl | White solid | 49–50° C. | | 21.0 (21.0) | 97.3 |
| 26 | p-F | Neophyl | 1 | Cl | Colorless liquid | | 1.5824 | 23.0 (23.0) | 99.3 |
| 27 | m-F | Neophyl | 1 | Cl | Colorless liquid | | 1.5829 | 23.1 (23.0) | 97.1 |
| 28 | o-CF₃ | n-Butyl | 1 | Cl | Colorless liquid | | 1.5005 | 28.1 | 95.0 |

TABLE 1-1-continued

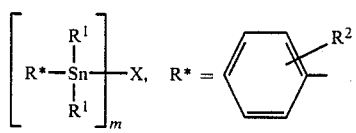

| Compound No. | R² | R¹ | m | X | Appearance | m.p. or b.p. | n³⁰ | Tin content | GLC purity (%) |
|---|---|---|---|---|---|---|---|---|---|
| 29 | p-F | n-Butyl | 1 | Cl | Colorless liquid | 160–165° C./ 4–6 mmHg | 1.5249 | 32.2 (28.7) | 96.2 |
| 30 | p-F | n-Octyl | 1 | Cl | Colorless liquid | | 1.5041 | 25.1 (32.7) | 96.2 |
| 31 | p-F | Cyclohexyl | 1 | Cl | White solid | 52–55° C. | | 28.6 (25.0) | 98.7 |
| 32 | m-CF₃ | Cyclohexyl | 1 | Cl | Pale yellow liquid | | 1.5352 | 24.5 (28.6) | 98.4 |
| 33 | o-CF₃ | Neophyl | 1 | —OCOMe | Viscous liquid | | 1.5535 | 20.0 (25.5) | |
| 34 | p-F | Neophyl | 1 | —OCOMe | Viscous liquid | | 1.5669 | 22.5 (25.1) | |
| 35 | m-F | Neophyl | 1 | —OCOMe | Viscous liquid | | 1.5675 | 22.4 (22.0) | |
| 36 | o-CF₃ | n-Butyl | 1 | —OCOMe | Viscous liquid | | 1.4851 | 26.5 (22.0) | |
| 37 | m-CF₃ | n-Butyl | 1 | —OCOMe | Colorless solid | 75–78° C. | | 27.3 (27.2) | |
| 38 | p-F | n-Butyl | 1 | —OCOMe | Colorless solid | 83–85° C. | | 31.1 (27.2) | |
| 39 | p-F | n-Octyl | 1 | —OCOMe | Colorless solid | 27–30° C. | | 24.0 (30.7) | |
| 40 | p-F | Cyclohexyl | 1 | —OCOMe | Colorless solid | 48–50° C. | | 27.5 (23.8) | |
| 41 | o-CF₃ | Neophyl | 1 | —SSCN(Me)₂ | Colorless solid | 102–105° C. | | 18.5 (27.0) | |
| 42 | p-F | Neophyl | 1 | —SSCN(Me)₂ | Colorless solid | 74–76° C. | | 19.6 (18.3) | |
| 43 | m-F | Neophyl | 1 | —SSCN(Me)₂ | Solid | | | 20.3 (20.2) | |
| 44 | o-CF₃ | n-Butyl | 1 | —SSCN(Me)₂ | Colorless solid | 28–30° C. | | 23.9 (20.2) | |
| 45 | m-CF₃ | n-Butyl | 1 | —SSCN(Me)₂ | Yellow liquid | | 1.5611 | 23.8 (23.8) | |
| 46 | p-F | n-Butyl | 1 | —SSCN(Me)₂ | Pale yellow liquid | | 1.5880 | 26.5 (23.8) | |
| 47 | p-F | n-Octyl | 1 | —SSCN(Me)₂ | Pale yellow liquid | | 1.5510 | 21.2 (26.5) | |
| 44 | p-F | Cyclohexyl | 1 | —SSCN(Me)₂ | Colorless solid | 101–105° C. | | 24.2 (21.2) | |
| 49 | p-F | Neophyl | 1 | 1,2,4-Triazol-1-yl | Colorless solid | 134–137° C. | | 21.0 (23.7) | |
| 50 | m-F | Neophyl | 1 | 1,2,4-Triazol-1-yl | Colorless solid | 154–157° C. | | 21.6 (21.6) | |
| 51 | p-F | n-Butyl | 1 | 1,2,4-Triazol-1-yl | Colorless solid | 68–72° C. | | 28.7 (21.6) | |
| 52 | m-CF₃ | n-Butyl | 1 | 1,2,4-Triazol-1-yl | Viscous liquid | | 1.5205 | 26.0 (30.0) | |
| 53 | p-F | n-Octyl | 1 | 1,2,4-Triazol-1-yl | Viscous liquid | | 1.5220 | 22.8 (26.6) | |
| 54 | p-F | Neophyl | 1 | 1,3-Imidazol-1-yl | Colorless solid | 123–127° C. | | 21.2 (23.4) | |
| 55 | o-CF₃ | Neophyl | 2 | —OSO₂O— | Viscous liquid | | 1.5700 | 21.0 (21.7) | |
| 56 | p-F | Neophyl | 2 | —OSO₂O— | Viscous liquid | | 1.5961 | 23.0 (20.5) | |
| 57 | o-CF₃ | Neophyl | 2 | —S— | Viscous liquid | | 1.6029 | 20.9 (22.5) | |
| 58 | p-F | Neophyl | 2 | —S— | Viscous liquid | | 1.6155 | 23.1 (21.7) | |
| 59 | o-CF₃ | Neophyl | 1 | —NCS | Liquid | | 1.5787 | 20.5 (23.9) | |
| 60 | o-CF₃ | Neophyl | 1 | —NCO | Liquid | | 1.5609 | 21.0 (20.2) | |
| 61 | o-CF₃ | Neophyl | 1 | —OCC₁₁H₂₃ (O=) | Liquid | | 1.5279 | 16.5 (20.7) | |

TABLE 1-1-continued

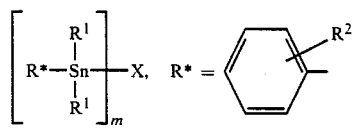

$$\left[\begin{array}{c} R^1 \\ | \\ R^*{-}Sn{-} \\ | \\ R^1 \end{array}X\right]_m, \quad R^* = \right.$$

| Compound No. | R² | R¹ | m | X | Appearance | m.p. or b.p. | n³⁰ | Tin content | GLC purity (%) |
|---|---|---|---|---|---|---|---|---|---|
| 62 | o-CF₃ | Neophyl | 1 | —OCC(Me)₃ (‖O) | Liquid | | 1.5414 | 18.6 (18.8) | |
| 63 | o-CF₃ | Neophyl | 2 | —OCCHBr / —OCCHBr (‖O, ‖O) | Solid | 128–131° C. | | 17.5 (17.6) | |
| 64 | o-CF₃ | Neophyl | 1 | —SCH₂COO-n-Bu | Liquid | | 1.5632 | | |
| 65 | o-CF₃ | Neophyl | 1 | —SCH₂COO-n-Oct | Liquid | | 1.5499 | | |
| 66 | o-CF₃ | Neophyl | 1 | 1,3-Imidazol-1-yl | Viscous liquid | | 1.5686 | 19.7 (19.9) | |
| 67 | o-CF₃ | Neophyl | 1 | —SMe | Viscous liquid | | 1.5804 | 20.9 (20.6) | |
| 68 | o-CF₃ | Neophyl | 1 | Phenoxy | Solid | 69–71° C. | | 19.1 (19.0) | |
| 69 | o-CF₃ | Neophyl | 1 | Phenylthio | Solid | 81–82° C. | | 18.7 (18.6) | |
| 70 | o-CF₃ | Neophyl | 1 | —OP(OBu)₂ (‖O) | Solid | 63–69° C. | | | |
| 71 | o-CF₃ | Neophyl | 1 | —SP(OEt)₂ (‖S) | Viscous liquid | | 1.5759 | | |
| 72 | 3-CF₃ 4-Cl | Neophyl | 1 | F | Solid | 50–56° C. | | 20.6 (20.3) | |
| 73 | 3-CF₃ 4-Cl | Neophyl | 1 | Cl | Solid | 69–71° C. | | 20.9 (19.8) | 99.0 |
| 74 | 3-CF₃ 4-Cl | Neophyl | 1 | Br | Solid | 72–74° C. | | 18.3 (18.4) | 99.0 |
| 75 | 3-CF₃ 4-Cl | Neophyl | 2 | —O— | Solid | 58–61° C. | | 20.4 (20.7) | |
| 76 | 3-CF₃ 4-Cl | Neophyl | 1 | —OAc | Solid | 60–62° C. | | 19.2 (19.0) | |
| 77 | 3-CF₃ 4-Cl | Neophyl | 1 | —SSCN(Me)₂ | Solid | 86–88° C. | | 17.6 (17.3) | |
| 78 | 3-CF₃ 4-Cl | Neophyl | 1 | 1,2,4-Triazol-1-yl | Solid | 159–161° C. | | 18.7 (18.8) | |
| 79 | 2,4-Difluoro | Neophyl | 1 | F | Solid | 60–63° C. | | 22.6 (22.9) | |
| 80 | 2,4-Difluoro | Neophyl | 1 | Cl | Liquid | | 1.5730 | 21.9 (22.2) | 98.1 |
| 81 | 2,4-Difluoro | Neophyl | 2 | —O— | Viscous liquid | | 1.5821 | 23.1 (23.4) | |
| 82 | 2,4-Difluoro | Neophyl | 1 | —OAc | Viscous liquid | | 1.5598 | 21.3 (21.3) | |
| 83 | 2,4-Difluoro | Neophyl | 1 | —SSCN(Me)₂ | Viscous liquid | | 1.6156 | 19.1 (19.2) | |
| 84 | 2,4-Difluoro | Neophyl | 1 | 1,2,4-Triazol-1-yl | Solid | 131–134° C. | | 20.9 (21.0) | |
| 85 | 3,4-Difluoro | Neophyl | 1 | F | Liquid | | 1.5793 | 23.2 (22.9) | |
| 86 | 3,4-Difluoro | Neophyl | 1 | Cl | Liquid | | 1.5745 | 22.1 (22.2) | 96.9 |
| 87 | 3,4-Difluoro | Neophyl | 2 | —O— | Viscous liquid | | 1.5820 | 23.3 (23.4) | |
| 88 | 3,4-Difluoro | Neophyl | 1 | —OAc | Solid | 33–35° C. | | 21.3 (21.3) | |
| 89 | 3,4-Difluoro | Neophyl | 1 | —SSCN(Me)₂ | Solid | 92–94° C. | | 19.5 (19.2) | |
| 90 | 3,4-Difluoro | Neophyl | 1 | 1,2,4-Triazol-1-yl | Solid | 50–53° C. | | 20.8 (21.0) | |
| 91 | 2,4,5-Trifluoro | Neophyl | 1 | F | Liquid | | 1.5644 | 22.0 (22.2) | |

TABLE 1-1-continued

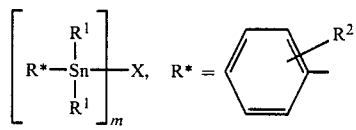

| Compound No. | R² | R¹ | m | X | Appearance | m.p. or b.p. | $n^{30}$ | Tin content | GLC purity (%) |
|---|---|---|---|---|---|---|---|---|---|
| 92 | 2,4,5-Trifluoro | Neophyl | 1 | Cl | Solid | 65–67° C. | | 21.7 (21.5) | 99.9 |
| 93 | 2,4,5-Trifluoro | Neophyl | 2 | —O— | Viscous liquid | | 1.5729 | 22.4 (22.6) | |
| 94 | 2,4,5-Trifluoro | Neophyl | 1 | —OAc | Solid | 59–61° C. | | 20.8 (20.6) | |
| 95 | 2,4,5-Trifluoro | Neophyl | 1 | —SSCN(Me)₂ | Solid | 81–83° C. | | 18.7 (18.7) | |
| 96 | 2,4,5-Trifluoro | Neophyl | 1 | 1,2,4-Triazol-1-yl | Solid | 125–130° C. | | 20.2 (20.3) | |
| 97 | o-Cl | Neophyl | 1 | F | Solid | 72–74° C. | | 23.2 (23.0) | |
| 98 | o-Cl | Neophyl | 1 | Cl | Viscous liquid | | 1.5981 | 22.2 (22.3) | |
| 99 | o-Cl | Neophyl | 2 | —O— | Viscous liquid | | 1.6070 | 23.4 (23.5) | |
| 100 | o-Cl | Neophyl | 1 | —OAc | Viscous liquid | | 1.5800 | 21.2 (21.4) | |
| 101 | o-Cl | Neophyl | 1 | —SSCN(Me)₂ | Solid | 100–103° C. | | 19.1 (18.7) | |
| 102 | m-Cl | Neophyl | 1 | F | Solid | 58–62° C. | | 23.1 (23.0) | |
| 103 | m-Cl | Neophyl | 1 | Cl | Solid | 41–43° C. | | 22.3 (22.3) | 96.3 |
| 104 | m-Cl | Neophyl | 2 | —O— | Viscous liquid | | 1.6048 | 23.6 (23.5) | |
| 105 | m-Cl | Neophyl | 1 | —OAc | Viscous liquid | | 1.5801 | 21.5 (21.4) | |
| 106 | m-Cl | Neophyl | 1 | —SSCN(Me)₂ | Viscous liquid | | 1.6326 | 19.0 (19.2) | |
| 107 | m-Cl | Neophyl | 1 | 1,2,4-Triazol-1-yl | Solid | 165–169° C. | | 21.1 (21.0) | |
| 108 | p-Cl | Neophyl | 1 | F | Solid | 104–105° C. | | 23.0 (23.0) | |
| 109 | p-Cl | Neophyl | 1 | Cl | Solid | 70–72° C. | | 22.6 (22.3) | 99.0 |
| 110 | p-Cl | Neophyl | 2 | —O— | Viscous liquid | | 1.6045 | 23.4 (23.5) | |
| 111 | p-Cl | Neophyl | 1 | —OAc | Viscous liquid | | 1.5808 | 21.5 (21.4) | |
| 112 | p-Cl | Neophyl | 1 | —SSCN(Me)₂ | Solid | 89–92° C. | | 19.3 (19.2) | |
| 113 | p-Cl | Neophyl | 1 | 1,2,4-Triazol-1-yl | Solid | 70–73° C. | | 20.8 (21.0) | |
| 114 | p-Me | Neophyl | 1 | F | Viscous liquid | | 1.5925 | 24.2 (24.0) | |
| 115 | p-Me | Neophyl | 1 | Cl | Solid | 34.5–35.5° C. | | 23.5 (23.2) | 96.7 |
| 116 | p-Me | Neophyl | 2 | —O— | Viscous liquid | | 1.6013 | 24.4 (24.5) | |
| 117 | p-Me | Neophyl | 1 | —OAc | Viscous liquid | | 1.5780 | 22.4 (22.2) | |
| 118 | p-Me | Neophyl | 1 | —SSCN(Me)₂ | Solid | 126–128° C. | | 20.1 (19.9) | |
| 119 | p-Me | Neophyl | 1 | 1,2,4-Triazol-1-yl | Solid | 103–108° C. | | 21.5 (21.8) | |
| 120 | m-Me | Neophyl | 1 | F | Solid | 58–59° C. | | 24.0 (24.0) | |
| 121 | m-Me | Neophyl | 1 | Cl | Viscous liquid | | 1.5893 | 23.5 (23.2) | 98.2 |
| 122 | m-Me | Neophyl | 2 | —O— | Viscous liquid | | 1.5969 | 24.8 (24.5) | |
| 123 | m-Me | Neophyl | 1 | —OAc | Viscous liquid | | 1.5748 | 22.5 (22.2) | |
| 124 | m-Me | Neophyl | 1 | —SSCN(Me)₂ | Solid | 51–54° C. | | 20.1 (19.9) | |
| 125 | m-Me | Neophyl | 1 | 1,2,4-Triazol-1-yl | Solid | 130–135° C. | | 21.5 (21.8) | |
| 126 | p-Me | Neophyl | 1 | F | Solid | 95–98° C. | | 24.1 (24.0) | |

TABLE 1-1-continued $$\left[ R^*-\underset{\underset{R^1}{|}}{\overset{\overset{R^1}{|}}{Sn}}\right]_m X, \quad R^* = \text{(phenyl with } R^2 \text{)}$$

| Compound No. | R² | R¹ | m | X | Appearance | m.p. or b.p. | n³⁰ | Tin content | GLC purity (%) |
|---|---|---|---|---|---|---|---|---|---|
| 127 | p-Me | Neophyl | 1 | Cl | Solid | 51–53° C. | | 23.3 (23.2) | 99.3 |
| 128 | p-Me | Neophyl | 2 | —O— | Viscous liquid | | 1.5982 | 24.7 (24.5) | |
| 129 | p-Me | Neophyl | 1 | —OAc | Viscous liquid | | 1.5755 | 22.4 (22.2) | |
| 130 | p-Me | Neophyl | 1 | —SSCN(Me)₂ | Solid | 92–94° C. | | 20.2 (19.9) | |
| 131 | p-Me | Neophyl | 1 | 1,2,4-Triazol-1-yl | Solid | 146–148° C. | | 21.5 (21.8) | |
| 132 | o-OMe | Neophyl | 1 | F | Viscous liquid | | 1.5885 | 23.0 (23.2) | |
| 133 | o-OMe | Neophyl | 1 | Cl | Solid | 69–72° C. | | 22.7 (22.5) | 99.5 |
| 134 | o-OMe | Neophyl | 2 | —O— | Viscous liquid | | 1.6013 | 24.1 (23.7) | |
| 135 | o-OMe | Neophyl | 1 | —OAc | Viscous liquid | 93–96° C. | 1.5756 | 21.8 (21.5) | |
| 136 | o-OMe | Neophyl | 1 | —SSCN(Me)₂ | Solid | 93–96° C. | | 19.6 (19.4) | |
| 137 | o-OMe | Neophyl | 1 | 1,2,4-Triazol-1-yl | Solid | 107–113° C. | | 21.3 (21.2) | |
| 138 | p-OMe | Neophyl | 1 | F | Viscous liquid | | 1.5943 | 23.4 (23.2) | |
| 139 | p-OMe | Neophyl | 1 | Cl | Viscous liquid | | 1.5918 | 22.7 (22.5) | 96.2 |
| 140 | p-OMe | Neophyl | 2 | —O— | Viscous liquid | | 1.6004 | 23.5 (23.7) | |
| 141 | p-OMe | Neophyl | 1 | —OAc | Viscous liquid | | 1.5777 | 21.9 (21.5) | |
| 142 | p-OMe | Neophyl | 1 | —SSCN(Me)₂ | Viscous liquid | | 1.6281 | 19.0 (19.4) | |
| 143 | p-OMe | Neophyl | 1 | 1,2,4-Triazol-1-yl | Solid | 134–140° C. | | 21.4 (21.2) | |
| 144 | H | Neophyl | 1 | F | Solid | 37–40° C. | | 24.9 (24.7) | |
| 145 | H | Neophyl | 1 | Cl | Viscous liquid | | 1.5937 | 24.3 (23.9) | 97.1 |
| 146 | H | Neophyl | 2 | —O— | Viscous liquid | | 1.6021 | 24.8 (25.2) | |
| 147 | H | Neophyl | 1 | —OAc | Viscous liquid | | 1.5769 | 23.1 (22.8) | |
| 148 | H | Neophyl | 1 | —SSCN(Me)₂ | Viscous liquid | | 1.6343 | 20.6 (20.4) | |
| 149 | H | Neophyl | 1 | 1,2,4-Triazol-1-yl | Solid | 130–135° C. | | 22.5 (22.4) | |
| 150 | o-CF₃ | Cyclohexyl | 1 | F | Solid | 98–102° C. | | 25.9 (26.4) | |
| 151 | o-CF₃ | Cyclohexyl | 1 | Cl | Solid | 51–52° C. | | 25.4 (25.5) | 98.6 |
| 152 | o-CF₃ | Cyclohexyl | 2 | —O— | Solid | 125–128° C. | | 26.2 (27.1) | |
| 153 | o-CF₃ | Cyclohexyl | 1 | —OAc | Liquid | | 1.5250 | 23.8 (24.3) | |
| 154 | o-CF₃ | Cyclohexyl | 1 | —OCC(Me)₃ ‖ O | Liquid | | 1.5111 | 21.8 (22.3) | |
| 155 | o-CF₃ | Cyclohexyl | 1 | —SCH₂COO-n-Bu | Liquid | | 1.5400 | | |
| 156 | o-CF₃ | Cyclohexyl | 1 | —SCH₂COO-n-Oct | Liquid | | 1.5312 | | |
| 157 | o-CF₃ | Cyclohexyl | 1 | —SSCN(Me)₂ | Solid | 154–156° C. | | 21.7 (21.7) | |
| 158 | o-CF₃ | Cyclohexyl | 1 | 1,2,4-Triazol-1-yl | Solid | 176–180° C. | | 23.5 (23.8) | |
| 159 | m-CF₃ | Cyclohexyl | 2 | —O— | Solid | 84–86° C. | | 26.9 (27.1) | |
| 160 | m-CF₃ | Cyclohexyl | 1 | —OAc | Solid | 59–61° C. | | 25.0 (24.3) | |
| 161 | m-CF₃ | Cyclohexyl | 1 | —SSCN(Me)₂ | Solid | 124–126° C. | | 21.6 | |

TABLE 1-1-continued

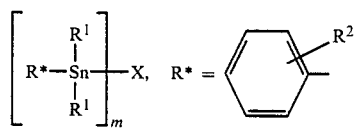

| Compound No. | R² | R¹ | m | X | Appearance | m.p. or b.p. | n³⁰ | Tin content | GLC purity (%) |
|---|---|---|---|---|---|---|---|---|---|
| 162 | m-CF₃ | Cyclohexyl | 1 | 1,2,4-Triazol-1-yl | Solid | 191–184° C. | | 22.9 (21.6) | |
| 163 | p-CF₃ | Cyclohexyl | 1 | F | Solid | 240° C. (decomp.) | | 26.4 (23.8) | |
| 164 | p-CF₃ | Cyclohexyl | 1 | Cl | Solid | 74–75° C. | | 25.8 (26.4) | 99.0 |
| 165 | p-CF₃ | Cyclohexyl | 2 | —O— | Solid | 86–89° C. | | 26.8 (25.5) | |
| 166 | p-CF₃ | Cyclohexyl | 1 | —OAc | Solid | 68–71° C. | | 23.9 (27.1) | |
| 167 | p-CF₃ | Cyclohexyl | 1 | —SCH₂COO-n-Bu | Liquid | | 1.5337 | 20.4 (24.3) | |
| 168 | p-CF₃ | Cyclohexyl | 1 | —SSCN(Me)₂ | Solid | 85–87° C. | | 21.7 (20.6) | |
| 169 | p-CF₃ | Cyclohexyl | 1 | 1,2,4-Triazol-1-yl | Solid | 215–225° C. | | 23.4 (21.6) | |
| 170 | m-F | Cyclohexyl | 1 | F | Solid | 225° C. (decomp.) | | 29.6 (23.8) | |
| 171 | m-F | Cyclohexyl | 1 | Cl | Solid | 52–53° C. | | 28.7 (29.7) | |
| 172 | m-F | Cyclohexyl | 2 | —O— | Solid | 44–46° C. | | 31.0 (28.6) | |
| 173 | m-F | Cyclohexyl | 1 | —OAc | Solid | 52–54° C. | | 27.1 (30.6) | |
| 174 | m-F | Cyclohexyl | 1 | —SCH₂COO-n-Bu | Liquid | | 1.5555 | 22.9 (27.0) | |
| 175 | m-F | Cyclohexyl | 1 | —SSCN(Me)₂ | Solid | 110–112° C. | | 24.0 (22.5) | |
| 176 | m-F | Cyclohexyl | 1 | 1,2,4-Triazol-1-yl | Solid | 208° C. (decomp.) | | 26.7 (23.7) | |
| 177 | o-CF₃ | Neophyl | 1 | —SSCN(Et)₂ | Liquid | | 1.5931 | 17.2 (26.5) | |
| 178 | o-CF₃ | Neophyl | 1 | o-t-Butylphenoxy | Solid | 75–76° C. | | 17.5 (17.5) | |
| 179 | o-CF₃ | Neophyl | 1 | 2,6-Diisopropylphenoxy | Liquid | | 1.5619 | 16.7 (17.5) | |
| 180 | o-CF₃ | Cyclohexyl | 1 | —SSCN(Et)₂ | Solid | 105–107° C. | | 20.6 (16.8) | |
| 181 | o-CF₃ | Cyclohexyl | 1 | o-t-Butylphenoxy | Liquid | | 1.5519 | 19.9 (20.5) | |
| 182 | o-CF₃ | Cyclohexyl | 1 | 2,6-Diisopropylphenoxy | Solid | 53–57° C. | | 19.3 (20.5) | |
| 183 | p-Cl | Cyclohexyl | 1 | F | Solid | 256–258° C. | | 28.2 (19.5) | |
| 184 | p-Cl | Cyclohexyl | 1 | Cl | Solid | 49–50° C. | | 27.1 (28.6) | |
| 185 | p-Cl | Cyclohexyl | 2 | —O— | Solid | 111–113° C. | | 29.4 (27.5) | |
| 186 | p-Cl | Cyclohexyl | 1 | —OAc | Solid | 97–99° C. | | 26.4 (29.3) | |
| 187 | p-Cl | Cyclohexyl | 1 | —SCH₂COO-n-Bu | Liquid | | 1.5645 | 21.9 (26.1) | |
| 188 | p-Cl | Cyclohexyl | 1 | —SSCN(Me)₂ | Solid | 70–73° C. | | 22.5 (21.8) | |
| 189 | p-Cl | Cyclohexyl | 1 | 1,2,4-Triazol-1-yl | Solid | 217–223° C. | | 25.5 (23.0) | |
| 190 | 3,4-Dichloro | Cyclohexyl | 1 | F | Solid | 193° C. (decomp.) | | 26.0 (25.5) | |
| 191 | 3,4-Dichloro | Cyclohexyl | 1 | Cl | Liquid | | 1.5903 | 25.1 (26.4) | 97.2 |
| 192 | 3,4-Dichloro | Cyclohexyl | 2 | —O— | Solid | 129–130° C. | | 27.4 (25.4) | |
| 193 | 3,4-Dichloro | Cyclohexyl | 1 | —OAc | Solid | 99–101° C. | | 24.4 (27.0) | |
| 194 | 3,4-Dichloro | Cyclohexyl | 1 | —SSCN(Me)₂ | Solid | 138–140° C. | | 21.5 (24.2) | |
| 195 | 3,4-Dichloro | Cyclohexyl | 1 | 1,2,4-Triazol-1-yl | Solid | 207–213° C. | | 24.0 (21.5) | |
| 196 | p-Me | Cyclohexyl | 1 | F | Solid | 245–247° C. | | 29.7 (23.8) | |

TABLE 1-1-continued

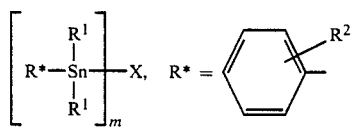

| Compound No. | R² | R¹ | m | X | Appearance | m.p. or b.p. | $n^{30}$ | Tin content | GLC purity (%) |
|---|---|---|---|---|---|---|---|---|---|
| 197 | p-Me | Cyclohexyl | 1 | Cl | Liquid | | 1.5705 | 28.6 (30.0) | |
| 198 | p-Me | Cyclohexyl | 2 | —O— | Solid | 71–73° C. | | 31.0 (28.8) | |
| 199 | p-Me | Cyclohexyl | 1 | —OAc | Solid | 83–85° C. | | 27.6 (30.9) | |
| 200 | p-Me | Cyclohexyl | 1 | —SCH₂COO-n-Bu | Liquid | | 1.5605 | 22.9 (27.3) | |
| 201 | p-Me | Cyclohexyl | 1 | —SSCN(Me)₂ | Solid | 92–94° C. | | 23.8 (22.7) | |
| 202 | p-Me | Cyclohexyl | 1 | 1,2,4-Triazol-1-yl | Solid | 205–210° C. | | 26.5 (23.9) | |
| 203 | p-Methoxy | Cyclohexyl | 1 | F | Solid | 234–236° C. | | 29.4 (26.7) | |
| 204 | p-Methoxy | Cyclohexyl | 1 | Cl | Liquid | | 1.5749 | 27.6 (28.9) | 96.9 |
| 205 | p-Methoxy | Cyclohexyl | 2 | —O— | Solid | 65–69° C. | | 29.6 (27.8) | |
| 206 | p-Methoxy | Cyclohexyl | 1 | —OAc | Solid | 82–84° C. | | 26.7 (29.7) | |
| 207 | p-Methoxy | Cyclohexyl | 1 | —SCH₂COO-n-Bu | Liquid | | 1.5630 | 22.5 (26.3) | |
| 208 | p-Methoxy | Cyclohexyl | 1 | —SSCN(Me)₂ | Solid | 78–80° C. | | 23.1 (22.0) | |
| 209 | p-Methoxy | Cyclohexyl | 1 | 1,2,4-Triazol-1-yl | Solid | 202–207° C. | | 25.4 (23.2) (25.8) | |

TABLE 1-2

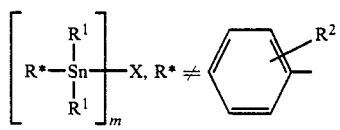

| Compound No. | R* | R¹ | m | X | Appearance | m.p. or b.p. | $n^{30}$ | Tin content (%) | GLC purity (%) |
|---|---|---|---|---|---|---|---|---|---|
| 210 | 2-Thienyl | Neophyl | 1 | Cl | Viscous liquid | | 1.5987 | 23.5 (23.6) | |
| 211 | 2-Thienyl | Neophyl | 2 | —O— | Solid | 90–99° C. | | 24.7 (24.9) | |
| 212 | 2-Thienyl | Neophyl | 1 | -OAC | Viscous liquid | | 1.5798 | 22.5 (22.6) | |
| 213 | 2-Thienyl | Neophyl | 1 | —SSCN(Me)₂ | Solid | 77–79° C. | | 20.4 (20.2) | |
| 214 | 2-Thienyl | Neophyl | 1 | 1,2,4-Triazol-1-yl | Solid | 147–157° C. | | 21.8 (22.1) | |
| 215 | 3-Thienyl | Neophyl | 1 | F | Solid | 85–90° C. | | 24.7 (24.4) | |
| 216 | 3-Thienyl | Neophyl | 1 | Cl | Viscous liquid | | 1.5988 | 23.9 (23.6) | 97.8 |
| 217 | 3-Thienyl | Neophyl | 2 | —O— | Solid | 78–81° C. | | 25.0 (24.9) | |
| 218 | 3-Thienyl | Neophyl | 1 | —OAc | Solid | 46–48° C. | | 22.7 (22.5) | |
| 219 | 3-Thienyl | Neophyl | 1 | —SSCN(Me)₂ | Solid | 87–89° C. | | 20.6 (20.2) | |
| 220 | 3-Thienyl | Neophyl | 1 | 1,2,4-Triazol-1-yl | Solid | 140–144° C. | | 21.9 (22.1) | |
| 221 | Trimethyl-silylmethyl | Neophyl | 1 | F | Liquid | | 1.5412 | | |
| 222 | Trimethyl-silylmethyl | Neophyl | 1 | Cl | Solid | 42.5–43.5° C. | | | 99.0 |
| 223 | Trimethyl-silylmethyl | Neophyl | 2 | —O— | Solid | 90.5–91.0° C. | | | |

TABLE 1-2-continued

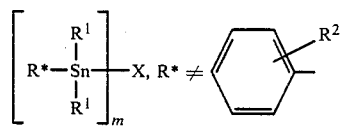

| Compound No. | R* | R¹ | m | X | Appearance | m.p. or b.p. | $n^{30}$ | Tin content (%) | GLC purity (%) |
|---|---|---|---|---|---|---|---|---|---|
| 224 | Trimethyl-silylmethyl | Neophyl | 1 | —OAc | Liquid | | 1.5372 | | |
| 225 | Trimethyl-silylmethyl | Neophyl | 1 | —SSCN(Me)₂ | Solid | 62–63° C. | | | |
| 226 | Trimethyl-silylmethyl | Neophyl | 1 | 1,2,4-Triazol-l-yl | Solid | 78–85° C. | | | |
| 227 | Dimethyl-phenylsilyl-methyl | Neophyl | 1 | Cl | Solid | 30° C. | | | 99.0 |
| 228 | Dimethyl-phenylsilyl-methyl | Neophyl | 2 | —O— | Solid | 87–89° C. | | | |
| 229 | Dimethyl-phenylsilyl-methyl | Neophyl | 1 | —OAc | Liquid | | 1.5617 | | |
| 230 | Dimethyl-phenylsilyl-methyl | Neophyl | 1 | —SSCN(Me)₂ | Liquid | | 1.6141 | | |
| 231 | Trimethyl-silylmethyl | Cyclo-hexyl | 1 | F | Solid | 167–170° C. | | | |
| 232 | Trimethyl-silylmethyl | Cyclo-hexyl | 1 | Cl | Solid | 74° C. | | | 99.0 |
| 233 | Trimethyl-silylmethyl | Cyclo-hexyl | 2 | —O— | Solid | 151–153° C. | | | |
| 234 | Trimethyl-silylmethyl | Cyclo-hexyl | 1 | —OAc | Solid | 52–53° C. | | | |
| 235 | Trimethyl-silylmethyl | Cyclo-hexyl | 1 | —SSCN(Me)₂ | Solid | 101–102° C. | | | |
| 236 | Trimethyl-silylmethyl | Cyclo-hexyl | 1 | 1,2,4-Triazol-l-yl | Solid | 197–201° C. (decomp.) | | | |
| 237 | Trimethyl-silylmethyl | Cyclo-hexyl | 1 | —OP(OBu)₂‖O | Solid | 130–132° C. | | | |
| 238 | Neopentyl | Neophyl | 1 | Cl | Solid | 65–66° C. | | 23.6 (24.1) | 99.9 |
| 239 | Neopentyl | Neophyl | 2 | —O— | Solid | 100–101° C. | | 25.7 (25.6) | |
| 240 | Neopentyl | Cyclo-hexyl | 1 | Cl | Solid | 106–107° C. | | 29.5 (30.3) | |
| 241 | Neopentyl | Cyclo-hexyl | 2 | —O— | Solid | 202–203° C. | | 32.5 (32.6) | |
| 242 | Dimethyl-phenylsilyl-methyl | Neophyl | 1 | F | Solid | 47–48° C. | | | |
| 243 | Dimethyl-phenylsilyl-methyl | Neophyl | 1 | 1,2,4-Triazol-1-yl | Solid | 66–71° C. | | | |
| 244 | Dimethyl-phenylsilyl-methyl | Neophyl | 1 | —OP(OBu)₂‖O | Liquid | | 1.5484 | | |
| 245 | Dimethyl-phenylsilyl-methyl | Cyclo-hexyl | 1 | F | Solid | 107–110° C. | | | |
| 246 | Dimethyl-phenylsilyl-methyl | Cyclo-hexyl | 1 | Cl | Liquid | | 1.5593 | | |
| 247 | Dimethyl-phenylsilyl-methyl | Cyclo-hexyl | 2 | —O— | Solid | 48–51° C. | | | |
| 248 | Dimethyl-phenylsilyl-methyl | Cyclo-hexyl | 1 | —OAc | Liquid | | 1.5421 | | |
| 249 | Dimethyl-phenylsilyl-methyl | Cyclo-hexyl | 1 | —SSCN(Me)₂ | Liquid | | 1.6054 | | |
| 250 | Dimethyl-phenylsilyl-methyl | Cyclo-hexyl | 1 | 1,2,4-Triazol-l-yl | Solid | 118–124° C. | | | |

TABLE 1-2-continued

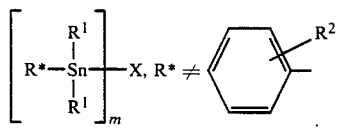

| Compound No. | R* | R¹ | m | X | Appearance | m.p. or b.p. | $n^{30}$ | Tin content (%) | GLC purity (%) |
|---|---|---|---|---|---|---|---|---|---|
| | methyl | | | | | | | | |
| 251 | Dimethyl-phenylsilyl-methyl | Cyclo-hexyl | 1 | $-\underset{\underset{O}{\|\|}}{O}P(OBu)_2$ | Solid | 125–126° C. | | | |

Various compounds to be employed in accordance with the present invention were formulated as wettable powders, emulsifiable concentrates, fine dusts, etc., as shown below.

| Ingredient | Part by weight |
|---|---|
| Formulation 1 Wettable powder | |
| Compound No. 28 | 50.0 |
| Clay | 40.5 |
| White carbon | 5.0 |
| Polyoxyalkylenealkyl-allylethersulfate | 3.0 |
| Alkylbenzensulfonate | 1.5 |
| Formulation 2 Emulsifiable concentrate | |
| Compound No. 25 | 25.0 |
| Alkylallylsulfonate | 3.0 |
| Polyoxyalkylenealkylallyl ether | 10.0 |
| Xylene | 42.0 |
| Dimethylformamide | 20.0 |

Compound No. 25, alkylalkylsulfonate and polyoxyalkylenealkylallyl ether are uniformly dissolved in xylene and dimethylformamide to obtain emulsifiable concentrate. The preparation is diluted with water when use.

| Formulation 3 Fine dust | |
|---|---|
| Compound No. 33 | 15.0 |
| White carbon | 20.0 |
| Isopropylazidophosphate | 0.3 |
| Fine clay | 64.7 |

The above ingredients are mixed and ground. The mixture is finely ground by Jetmizer grinder to obtain fine dust. The preparation is used as it is.

| Formulation 4 Dust | |
|---|---|
| Compound No. 49 | 5.0 |
| Clay | 91.7 |
| White carbon | 3.0 |
| Tall oil | 0.3 |

The above ingredients are mixed and ground to obtain dust preparation. The dust is used as it is.

Experiment 1

Sample

Compounds of the invention to be tested are dissolved in a minimum of DMF. Distilled water containing Tween 20 at the concentration of 100 ppm is thereto added to prepare a series of samples of the desired concentrations.

Test Procedure

A. Suppression of *Spodoptera litura* (common cutworm) larvae

Cabbage leaves (5×5 cm) were immersed in the sample solution as prepared above and air dried. Two leaves were placed in a petri dish (9 cm diameter) and 10 third-instar larvae of *Spodoptera litura* were placed in the dish. The dish was held at 25° C. and the mortality of the larvae was measured after 48 hours.

C. Suppression of *Plutella xylostella* (diamond backmoth) larvae

Cabbage leaf (7×7 cm) was immersed in the sample solution and air dried. The leaf was placed in a petri dish (9 cm diameter) and 10 third-instar larvae of *Plutella xylostella* were placed in the dish. The dish was held at 25° C. and the mortality of the larvae was measured after 48 hours.

D. Suppression of *Adoxophyes* sp. larvae

Whole tea leaves were immersed in the sample solution and air dried. Three leaves were placed in a polyethylene petri dish (6 cm diameter, 4 cm depth) and 10 forth-instar larvae of Adoxophyes sp. were placed in the dish. The dish was held at 25° C. and the mortality of the larvae was measured after 48 hours.

E. Suppression of *Nephotettix cincticeps* (green rice leaf hopper) (sensitive)

Six or seven rice seedlings of 1.5 to 2 plant age in leaf number were bundled and the roots were wrapped in sponge. The seedlings were placed in a polyethylene cup (diameter 6 cm, depth 4 cm) and the cup is placed in a rotary application tower, whereby the leaves and sheaths of the seedlings were sprayed with 2 ml of the sample solution and air dried. The treated seedlings were covered with a transparent plastic cylinder and ten female larvae were placed in the cylinder. The atmosphere in the cylinder was kept at 25° C., and the mortality after 48 hours was measured.

I. and J. Suppression of *Myzus persicae* (green peach aphid) larvae (I: sensitive, J: resistant)

A polyethylene cup (diameter 6 cm, depth 4 cm) was filled with 0.3% agar gel and a piece of Chinese cabbage leaf (3×3 cm) was placed on the gel. An apterous adult of *Myzus persicae* was placed on the cabbage and allowed to egg-deposit while keeping the surrounding atmosphere at 25° C. for 24 hours. After removing the adult, 2 ml of the sample was sprayed on the leaf under a rotary application tower. The test system was kept at 25° C. for 48 hours and the mortality of born larvae was measured.

M. Suppression of *Tetranychus cinnabrinus* (carmine spider mite)

A polyethylene cup (diameter 6 cm, depth 4 cm) was filled with 0.3% agar gel and a piece of bush bean leaf (diameter 2 cm) was placed on the gel. About twelve adults of *Tetranychus cinnabrinus* were placed on the leaf. After 24 hours at 25° C., dead and feeble adults were removed and 2 ml of the sample solution was sprayed on the leaf and audlts under a rotary application tower. Following such treatment the test system was kept at 25° C. and the mortality was measured after 48 hours.

O. Suppression of *Tetranychus urticae* (Two-spotted spider mite)

The same test procedure as above was repeated on *Tetranychus urticae*.

X. Suppression of *Tetranychus cinnabrinus* larvae

A polyethylene cup (diameter 6 cm, depth 4 cm) was filled with 0.3% agar gel and a piece of bush bean leaf (diameter 2 cm) was placed on the gel. Seven adults of *Tetranychus cinnabrinus* were placed on the leaf and allowed to egg-deposit while keeping the surrounding atmosphere at 25° C. for 24 hours. After removing the adult, 2 ml of the sample was sprayed on the leaf under a rotary application tower. The test system was kept at 25° C. for 7 days and the mortality of born larvae was measured.

Y. Suppression of *Tetranychus urticae* larvae

The same test procedure as above was repeated on *Tetranychus urticae* larvae.

N. Suppression of *Tetranychus cinnabrinus* eggs

P. Suppression of *Tetranychus urticae* eggs

The test procedure as described in X and Y were repeated on *Tetranychus cinnabrinus* and *urticae* eggs. The test system was kept at 25° C. for 7 days and the mortality of eggs was measured by counting the number of eggs which did not hatch.

T. Suppression of *Henosepilachna vigintioctopunctata* (twenty-eight-spotted beetle) adults Japanese eggplant leaf (6×6 cm) was immersed in the sample solution and air dired. The leaf was placed in a petri dish (9 cm diameter) and 5 adults of *Henosepilachna vigintioctopunctata* were placed in the dish. The dish was held at 25° C. and the mortality was measured after 48 hours.

R. Suppression of *Periplaneta americana* (American cockroach) larvae

A filter paper soaked with the sample solution was placed in a petri dish (diameter 9 cm). Five *Periplaneta americana* larvae with 7 days after hatching were placed in the dish hold at 25° C. and the mortality after 48 hours was measured.

W. Suppression of *Callosobruchus chinensis* (adzuki bean weevil)

Ten *Callosobruchus chinensis* adults within 24 hours after hatching were placed in a screw cylinder (diameter 1.8 cm, height 5 cm) with stainless nets at the up-and-down openings. The cylinder was submerged in the sample solution, and the adults exposed to the solution were air dried. The mortality was measured after 48 hours at 25° C.

K. Suppression of *Panonychus citri* (citrus red mite)

The same test procedure as M and O was repeated on *Panonychus citri* except that lemon leaf, rather than bush bean leaf, was employed.

Q. Suppression of *Tetranychus kanzawai* (kanzawa spider mite) (resistant adults)

The same test procedure as M and O was repeated on resistant adults of *Teranychus kanzawai*.

Test Results

Table 2 below shows the mortality (%) of various pests exposed to the indicated compounds (I) at several concentrations, wherein the following codes are employed for pests.

A: *Spodoptera litura* (larvae)
C: *Plutella xylostella* (larvae)
D: *Adoxophyes sp.* (larvae)
E: *Nephotettix cincticeps* (sensitive adults)
I: *Myzus persicae* (sensitive larvae)
J: *Myzus persicae* (resistant larvae)
K: *Panonychus citri* (adults)
L: *Panonychus citri* (eggs)
M: *Tetranychus cinnabrinus* (adults)
N: *Tetranychus cinnabrinus* (eggs)
O: *Tetranychus urticae* (adults)
P: *Tetranychus urticae* (eggs)
Q: *Tetranychus kanzawai* (resistant adults)
R: *Periplaneta americana* (larvae)
T: *Henosepilachna vigintioctopunctata* (adults)
W: *Callosobruchus chinensis* (adults)
X: *Tetranychus cinnabrinus* (eggs-larvae)
Y: *Tetranychus urticae* (eggs-larvae)

Table 2 also lits the test results on commercially available Osadan ® and Plictran ® employed as a control.

Resistance adults of *Tetranychus kanzawai* used in Test Q were those which acquired resistance against Osadan ® and Plictran ® and were gathered at Yaguchihara and Okadahara, Shizuoka, Japan. Test results on the adults from Yaguchihara and Okadahara are shown on the left and right, respectively, of column "Q" in Table 2.

TABLE 2

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| Osadan | 1000 |  |  |  |  |  |  |  |  |  |  | 100 | 93 |  |  | 47 | 52 |  |  | 100 | 100 |
|  | 250 |  |  |  |  |  |  |  |  |  |  | 100 |  | 95 |  | 37 | 36 |  |  | 100 | 80 |
|  | 63 |  |  |  |  |  |  |  |  |  |  | 90 |  |  |  | 27 | 16 |  |  |  |  |
| Plictran | 1000 | 100 |  |  |  |  |  |  |  |  |  | 100 |  | 100 |  | 51 | 69 |  |  | 100 | 100 |
|  | 250 | 100 |  |  |  |  |  |  |  |  |  | 100 |  | 93 |  | 23 | 36 |  |  | 100 | 50 |
|  | 63 | 100 |  |  |  |  |  |  |  |  |  | 88 |  |  |  | 10 | 24 |  |  | 40 |  |
|  | 15 |  |  |  |  |  |  |  |  |  |  |  |  |  |  | 1 | 3 |  |  |  |  |
| 1 | 1000 |  |  |  |  |  |  |  |  |  |  | 100 | 70 | 100 |  | 97 |  |  |  | 100 | 90 |
|  | 250 |  |  |  |  |  |  |  | 97 |  |  |  |  | 77 |  |  | 90 |  |  |  |  |
|  | 63 |  |  |  |  |  |  |  |  |  |  |  |  |  |  |  |  |  |  |  |  |
| 2 | 1000 | 100 |  |  |  |  |  |  |  |  |  | 100 |  | 100 |  |  |  |  |  | 100 | 100 |
|  | 250 | 100 |  |  |  |  |  |  |  |  |  | 100 |  | 97 |  |  |  |  |  |  | 70 |
|  | 63 | 70 |  |  |  |  |  |  |  |  |  | 100 |  |  |  |  |  |  |  |  |  |
| 3 | 1000 |  |  |  |  |  |  |  | 87 |  |  | 100 |  | 100 |  |  |  |  |  | 100 | 100 |
|  | 250 |  |  |  |  |  |  |  |  |  |  |  |  | 79 |  |  |  |  |  |  | 80 |
|  | 63 |  |  |  |  |  |  |  |  |  |  |  |  |  |  |  |  |  |  |  |  |
| 4 | 1000 |  |  |  |  |  | 100 |  |  |  |  | 100 | 70 | 100 |  |  |  |  |  | 100 | 100 |
|  | 250 |  |  |  |  |  |  |  | 91 |  |  |  |  | 76 |  |  | 70 |  |  |  | 80 |
|  | 63 |  |  |  |  |  |  |  |  |  |  |  |  |  |  |  |  |  |  |  |  |
| 5 | 1000 |  |  |  |  |  |  |  |  |  |  | 100 |  | 100 | 97 |  |  |  |  | 100 | 100 |
|  | 250 |  |  |  |  |  |  |  |  |  |  |  |  | 80 | 71 |  | 76 |  |  |  | 80 |
|  | 63 |  |  |  |  |  |  |  |  |  |  |  |  |  |  |  |  |  |  |  |  |
| 6 | 1000 |  |  |  |  |  |  | 100 |  | 97 |  | 100 | 81 | 100 |  |  |  |  |  | 100 | 100 |
|  | 250 |  |  |  |  |  |  | 92 |  | 89 |  |  |  | 72 |  |  |  |  |  |  | 80 |
|  | 63 |  |  |  |  |  |  |  |  |  |  |  |  |  |  |  |  |  |  |  |  |
| 7 | 1000 |  |  |  |  |  |  | 100 | 100 | 90 |  | 100 | 95 | 100 | 83 | 96 | 89 |  |  | 100 | 90 |
|  | 250 |  |  |  |  |  |  | 95 |  | 86 |  |  |  | 78 |  | 80 | 74 |  |  |  |  |
|  | 63 |  |  |  |  |  |  |  |  |  |  |  |  |  |  |  |  |  |  |  |  |
| 8 | 1000 |  |  |  |  |  |  |  | 100 | 95 |  | 100 | 70 | 100 | 79 | 100 | 93 |  |  | 100 | 100 |
|  | 250 |  |  |  |  |  |  |  |  |  |  |  |  | 100 |  | 79 |  |  |  |  |  |
|  | 63 |  |  |  |  |  |  |  |  |  |  |  |  |  |  |  |  |  |  |  |  |
| 9 | 1000 |  |  |  |  |  |  |  | 100 | 94 |  | 100 |  | 100 |  | 100 | 96 |  |  | 100 | 100 |
|  | 250 |  |  |  |  |  |  |  |  |  |  | 74 |  | 88 |  | 85 | 84 |  |  | 95 | 90 |
|  | 63 |  |  |  |  |  |  |  |  |  |  | 100 |  |  |  |  |  |  |  |  |  |
| 10 | 1000 |  |  |  | 72 |  |  |  |  | 97 |  | 100 |  | 100 | 95 | 96 | 96 |  |  | 100 | 100 |
|  | 250 |  |  |  |  |  |  |  |  |  |  |  |  | 93 |  |  |  |  |  |  | 70 |
|  | 63 |  |  |  |  |  |  |  |  |  |  |  |  |  |  |  |  |  |  |  |  |
| 11 | 1000 | 100 |  |  |  |  |  | 100 | 92 | 84 |  | 100 | 90 | 100 |  |  |  | 80 | 100 | 100 | 100 |
|  | 250 | 100 | 95 |  |  |  |  | 100 | 81 |  |  | 100 | 75 | 95 |  |  |  |  |  | 100 |  |
|  | 63 |  | 70 |  |  |  |  | 87 |  |  |  |  |  |  |  |  |  |  |  |  |  |
| 12 | 1000 | 100 |  |  |  |  |  |  |  |  |  | 100 | 100 |  |  |  |  |  |  | 100 | 80 |
|  | 250 | 90 | 90 |  |  |  |  |  |  |  |  | 93 |  |  |  |  |  |  |  | 95 |  |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 16 | 63 | | | | | | | | | | | | | | | | | | | | |
|  | 1000 | | | | | | | 100 | 100 | | | 100 | 87 | 100 | 88 | 100 76 | | | | 100 | 100 |
|  | 250 | | | | | | | 86 | | | | | | 100 | | 93 | | | | | |
|  | 63 | | | | | | | | | | | | | 92 | | 79 | | | | | |
|  | 16 | | | | | | | | | | | | | | | | | | | | |
| 17 | 1000 | | | | | | | | | | | 100 | | 100 | 86 | 97 | | | | 100 | 100 |
|  | 250 | | | | | | | | | | | 100 | 80 | 100 | | 81 89 | | | | 100 | 98 |
|  | 63 | | | | | | | | | | | | | 75 | | | | | | 85 | |
|  | 16 | | | | | | | | | | | | | | | | | | | 100 | |
| 18 | 1000 | | | | | | 100 | | | | | 100 | | 100 | 87 | 78 92 | | | | 100 | 100 |
|  | 250 | | | | | | | | | | | 100 | | 100 | 70 | 70 | | | | 100 | 100 |
|  | 63 | | | | | | | | | | | 73 | | 91 | | | | | | | 80 |
|  | 16 | | | | | | | | | | | 100 | | | | | | | | | |
| 19 | 1000 | 100 | | | | | | 100 | | | | 100 | 95 | | | | | | | | 100 |
|  | 250 | 80 | | | | | | 84 | 100 | 94 | | 100 | 92 | | | | | | | | |
|  | 63 | | | | | | | 81 | 86 | | | 100 | | | | | | | | | |
|  | 16 | | | | | | | | | | | 91 | | | | | | | | | |
| 20 | 1000 | 70 | | | | | | 100 | | | | 100 | 100 | 97 | | | | | | | 80 |
|  | 250 | | | | | | | | | | | 97 | | | | | | | | | |
|  | 63 | | | | | | | | | | | 80 | | | | | | | | | |
|  | 16 | | | | | | | | | | | 94 | | | | | | | | | |
| 23 | 1000 | 100 | | | | | | | 100 | | | 100 | 85 | | | | | | | | |
|  | 250 | 90 | | | | | | | | | | | | | | | | | | | |
|  | 63 | | | | | | | | | | | | | | | | | | | | |
|  | 16 | | | | | | | | | | | | | | | | | | | | |
| 25 | 1000 | | | | | | | 100 | | | | 100 | | 100 | | 100 | 80 | | | 100 | 100 |
|  | 250 | | | | | | | 94 | 93 | 97 | | 100 | 83 | 97 | 78 | 86 89 | | | | 70 | 80 |
|  | 63 | | | | | | | | | | | 92 | | | | | | | | | |
|  | 16 | | | | | | | | | | | 100 | | | | | | | | | |
| 21 | 1000 | 100 | 100 | | | | | 100 | 100 | | | 100 | 83 | 100 | | 100 | 100 | | | 100 | |
|  | 250 | 80 | | | | | | 100 | 73 | | | 100 | | 100 | 88 | 83 93 | | | | | |
|  | 63 | | | | | | | | | | | 91 | | | | | | | | | |
|  | 16 | | | | | | | | | | | | | | | | | | | | |
| 24 | 1000 | 75 | | | | | | 100 | | | | 100 | 100 | 100 | 71 | 97 | 80 | | | 98 | |
|  | 250 | | | | | | | | | | | | | | | | | | | | |
|  | 63 | | | | | | | | | | | | | | | | | | | | |
|  | 16 | | | | | | | | | | | | | | | | | | | | |
| 26 | 1000 | | | | | | | 100 | 100 | | | 100 | | 100 | | | | | 100 | 100 | 100 |
|  | 250 | | | | | | | | | | | 100 | | 100 | | | | | | | |
|  | 63 | | | | | | | | | | | | | | | | | | | | |
|  | 16 | | | | | | | | | | | | | | | | | | | | |
| 27 | 1000 | | | | | | | 100 | | | | 100 | 96 | 100 | 88 | | | 80 | | 100 | 100 |
|  | 250 | | | | | | | 100 | | | | 100 | | 100 | | | | | | 70 | 80 |
|  | 63 | | | | | | | | | | | | | 82 | | | | | | | |
|  | 16 | | | | | | | | | | | | | | | | | | | | |
| 28 | 1000 | | | | | | | 100 | | | | 100 | 85 | 100 | | | | | | 100 | 100 |
|  | 250 | | | | | | | 100 | | | | 100 | | 100 | | | | | | 100 | 100 |
|  | 63 | | | | | | | 95 | | | | 100 | | | | | | | | 85 | |
|  | 16 | | | | | | | | | | | | | | | | | | | 100 | |
| 29 | 1000 | 100 | | | | | | 100 | 100 | | | 100 | | | 100 | 100 | 100 | 100 | | 100 | 100 |
|  | 250 | 75 | | | | | | 100 | | | | 100 | | | | | | | | 100 | 95 |
|  | 63 | | | | | | | | | | | 97 | | | | | | | | | 70 |
|  | 16 | | | | | | | | | | | | | | | | | | | | |
| 30 | 1000 | | | | | | | 77 | | | | 100 | | | | | | | | 100 | 100 |
|  | 250 | | | | | | | | | | | | | | | | | | | | |
|  | 63 | | | | | | | | | | | | | | | | | | | | |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 31 | 1000 | 100 | | | | | | | | | | 93 | | | | | | | | 95 | |
|    | 250  | 95  | 85 | | | | | | | | | | | | | | | | | | |
|    | 63   |     | | | | | | | | | | | | | | | | | | | |
|    | 16   |     | | | | | | | | | | | | | | | | | | | |
| 32 | 1000 | 100 | | | | | | | | | | | | | | | | | | | 100 |
|    | 250  | 80  | 80 | | | | | | | | | | | | | | | | | 80 | |
| 33 | 1000 | | | | | | | 100 | | | | 100 | | 100 | | | | | | 100 | |
|    | 250  | | | | | | | 83  | | | | 100 | 94 | 100 | 70 | | | | | 100 | 100 |
|    | 63   | | | | | | | 100 | 100 | | | 100 | | 77 | | | | | | 80 | 98 |
|    | 16   | | | | | | | 93 | | | | | | | | | | | | | 80 |
| 34 | 1000 | 100 | | | | | | | | | | 100 | | 100 | | 100 | | | | 100 | 100 |
|    | 250  | 70  | 75 | | | | | | | | | 100 | 84 | 79 | | 86 | | | | 100 | 90 |
|    | 63   |     | | | | | | | | | | | | | 74 | 92 | | | | 80 | |
|    | 16   |     | | | | | | | | | | | | | | | | | | | |
| 35 | 1000 | 85 | | | | | | | | | | 100 | | 100 | | 100 | | | | 100 | 100 |
|    | 250  | | | | | | | | | | | | | 93 | | 83 | | | | | |
|    | 63   | | | | | | | | | | | | | | | 96 | | | | | |
|    | 16   | | | | | | | | | | | | | | | 79 | | | | | |
| 36 | 1000 | 100 | | | 84 | | | 100 | | | | 100 | 98 | 100 | | | | | | 100 | 100 |
|    | 250  | 70  | | | | | | 100 | | | | 100 | 85 | 100 | | | | | | 100 | 100 |
|    | 63   |     | | | | | | 74  | | | | 100 | | | | | | | | | |
|    | 16   |     | | | | | | 100 | | | | 93 | | | | | | | | | |
| 37 | 1000 | 85 | | | | | | | | | | 100 | 100 | 100 | 75 | | | | | 100 | 100 |
|    | 250  | | | | | | | | | | | 100 | 74 | 88 | | | | | | | |
| 38 | 1000 | 100 | | | | | | 100 | 100 | | | 100 | 95 | 100 | | | | | | 100 | |
|    | 250  | 95  | 75 | | | | | 100 | | | | 100 | | 100 | | | | | | | |
|    | 63   |     | | | | | | | | | | 84 | | | | | | | | | |
|    | 16   |     | | | | | | | | | | 100 | | | | | | | | | |
| 39 | 1000 | 100 | | | | | | 100 | | 94 | | 100 | 92 | 91 | | | | | | | |
|    | 250  | | | | | | | | | | | 87 | | | | | | | | | |
| 40 | 1000 | | | | | | | | | | | 100 | | 100 | | 85 | 100 | 100 | | 100 | 90 |
|    | 250  | | | | | | | | | | | | | 92 | | | | | | | |
| 41 | 1000 | | | | | | | | | | | 100 | 73 | 100 | | 100 | | | | 100 | 100 |
|    | 250  | | | | | | | | | 97 | | | | 88 | | | | | | | |
| 42 | 1000 | | | | | | | | | | | 100 | 72 | 100 | | 100 | | 100 | | 100 | 100 |
|    | 250  | | | | | | | | 90 | 97 | | 100 | 84 | 70 | | 96 | | 100 | | 100 | 98 |
|    | 63   | | | | | | | | | 91 | | 100 | | | | 71 | | | | 70 | |
| 43 | 1000 | | | | | | | | | | | 100 | | 91 | 92 | | | | | 100 | 100 |
|    | 250  | | | | | | | | | 90 | | 100 | | 97 | 71 | 89 | | | | 100 | 80 |
|    | 63   | | | | | | | | | | | 100 | | 84 | | | | | | | |
| 44 | 1000 | 100 | | | | | | 100 | | | | 100 | 100 | 100 | | | | | | 100 | 100 |
|    | 250  | 70  | | | | | | 100 | | | | 80  | 92 | 94 | | | | | | | |
|    | 63   |     | | | | | | | | | | | | | | | | | | | |
| 45 | 1000 | 100 | | | | | | 100 | 100 | | | 100 | 100 | 100 | | | | 100 | | 100 | |
|    | 250  |     | 80 | | | | | 84  | | | | 93 | 85 | 70 | | | | | | | |
|    | 63   |     | | | | | | | | | | 100 | | | | | | | | | |
| 46 | 1000 | 100 | | | | | | 100 | 100 | | | 100 | 82 | 100 | | | | | | 100 | 100 |
|    | 250  |     | | | | | | 100 | | | | 100 | | | | | | | | 80 | |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 47 | 63 |  |  |  |  |  |  | 100 | 69 |  |  | 97 |  | 100 |  |  |  |  |  |  |  |
|  | 1000 |  |  |  |  |  |  | 85 |  |  |  | 100 |  |  |  |  |  |  |  |  |  |
| 48 | 250 |  |  |  |  |  |  |  |  |  |  | 100 |  | 93 |  |  |  |  |  | 90 |  |
|  | 1000 | 100 |  |  |  |  |  |  |  |  |  | 100 |  |  |  |  |  |  |  | 100 | 100 |
|  | 250 |  |  |  |  |  |  |  |  |  |  | 85 |  | 88 |  |  |  |  |  | 100 | 95 |
| 49 | 63 |  |  |  |  |  |  |  |  |  | 90 | 71 |  |  |  |  |  |  |  |  |  |
|  | 1000 |  |  |  |  |  |  |  |  | 91 |  | 100 | 84 | 100 |  |  |  |  |  | 100 | 100 |
|  | 250 |  |  |  |  |  |  |  |  |  |  | 100 |  | 100 |  |  |  |  |  | 70 | 70 |
|  | 63 |  |  |  |  |  |  |  |  |  |  | 94 |  |  |  |  |  |  |  | 100 |  |
| 50 | 1000 |  |  |  |  |  |  |  |  |  |  | 100 |  | 100 |  |  |  |  |  |  | 95 |
|  | 250 |  |  |  |  |  |  |  |  | 82 |  | 100 |  | 97 |  |  |  |  |  |  |  |
|  | 63 |  |  |  |  |  |  |  |  |  |  | 100 |  | 82 |  |  |  |  |  |  |  |
|  | 16 |  |  |  |  |  |  |  |  |  |  | 94 |  |  | 82 |  |  |  |  |  |  |
| 51 | 1000 | 100 |  |  |  |  |  | 100 |  |  |  | 100 | 75 | 100 |  |  | 100 |  |  | 100 |  |
|  | 250 | 85 | 75 |  |  |  |  | 100 | 100 |  |  | 100 |  | 97 |  |  |  |  |  |  |  |
|  | 63 | 70 |  |  |  |  |  |  |  |  |  | 100 |  |  |  |  |  |  |  |  |  |
| 52 | 1000 | 100 |  |  |  |  |  | 100 |  |  |  | 100 | 100 | 100 |  |  |  |  |  | 100 | 100 |
|  | 250 | 80 | 80 |  |  |  |  |  | 75 |  |  | 100 |  | 89 |  |  |  |  |  |  |  |
|  | 63 |  |  |  |  |  |  |  |  |  |  | 94 |  |  |  |  |  |  |  |  |  |
| 54 | 1000 |  |  |  |  |  |  |  |  |  |  | 100 |  | 100 |  |  |  |  |  |  | 100 |
|  | 250 |  |  |  |  |  |  |  |  |  |  | 100 |  | 92 |  |  |  |  |  |  |  |
|  | 63 |  |  |  |  |  |  |  |  |  |  | 97 |  |  |  |  |  |  |  |  |  |
| 59 | 1000 |  |  |  |  |  |  |  |  |  |  |  |  | 100 |  |  |  |  |  |  | 100 |
|  | 250 |  |  |  |  |  |  |  |  |  |  |  |  | 100 |  |  |  |  |  |  |  |
| 60 | 1000 |  |  |  |  |  |  | 75 |  |  |  |  |  | 100 |  |  |  |  |  |  | 100 |
|  | 250 |  |  |  |  |  |  |  |  |  |  |  |  | 97 |  |  |  |  |  |  |  |
| 61 | 1000 |  |  |  |  |  |  |  |  |  |  |  |  | 100 |  |  |  |  |  |  | 100 |
|  | 250 |  |  |  |  |  |  |  |  |  |  |  |  | 89 |  |  |  |  |  |  |  |
| 62 | 1000 |  |  |  |  |  |  |  |  |  |  |  |  | 97 |  |  |  |  |  |  | 100 |
|  | 250 |  |  |  |  |  |  |  |  |  |  |  |  | 100 |  |  |  |  |  |  |  |
| 63 | 1000 |  |  |  |  |  |  |  |  |  |  |  |  | 100 |  |  |  |  |  |  | 90 |
|  | 250 |  |  |  |  |  |  |  |  |  |  |  |  | 92 |  |  |  |  |  |  | 80 |
| 64 | 1000 |  |  |  |  |  |  | 72 |  |  |  |  |  | 100 |  |  |  |  |  |  | 70 |
|  | 250 |  |  |  |  |  |  |  |  |  |  |  |  | 100 |  |  |  |  |  |  |  |
| 65 | 1000 |  |  |  |  |  |  |  |  |  |  |  |  | 100 |  |  |  |  |  |  | 90 |
| 66 | 1000 |  |  |  |  |  |  |  |  |  |  |  |  | 100 |  |  |  |  |  |  |  |
| 67 | 250 |  |  |  |  |  |  |  |  |  |  |  |  |  |  |  |  |  |  |  | 90 |
| 68 | 1000 |  |  |  |  |  |  |  |  |  |  |  |  | 83 |  |  |  |  |  |  |  |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| | 250 | | | | | | | 90 | | | | | | | | | | | | | 100 |
| | 63 | | | | | | | | | | | | | | | | | | | | |
| 69 | 16 | | | | | | | | | | | | | 100 | | | | | | | |
| | 1000 | | | | | | | | | | | | | 100 | | | | | | | 100 |
| | 250 | | | | | | | | | | | | | 71 | | | | | | | |
| | 63 | | | | | | | | | | | | | | | | | | | | |
| 70 | 1000 | | | | | | | | | | | | | 100 | | | | | | | 100 |
| | 250 | | | | | | | | | | | | | 94 | | | | | | | |
| | 63 | | | | | | | | | | | | | | | | | | | | |
| 71 | 1000 | | | | | | | | | | | | | 100 | | | | | | | 100 |
| | 250 | | | | | | | | | | | | | 81 | | | | | | | |
| | 63 | | | | | | | | | | | | | | | | | | | | |
| 72 | 1000 | | | | | | | | | | | | | 100 | | | | | | | 100 |
| | 250 | | | | | | | | | | | | | 97 | | | | | | | |
| | 63 | | | | | | | | | | | | | | | | | | | | |
| 73 | 1000 | | | | | | | | | | | | | 100 | | | | | | | 100 |
| | 250 | | | | | | | | | | | | | 84 | | | | | | | |
| | 63 | | | | | | | | | | | | | | | | | | | | |
| 74 | 1000 | | | | | | | | | | | | | 100 | | | | | | | 100 |
| | 250 | | | | | | | | | | | | | 82 | | | | | | | |
| | 63 | | | | | | | | | | | | | | | | | | | | |
| 75 | 1000 | | | | | | | | | | | | | 100 | | | | | | | 100 |
| | 250 | | | | | | | | | | | | | 88 | | | | | | | |
| | 63 | | | | | | | | | | | | | | | | | | | | |
| 76 | 1000 | | | | | | | | | | | | | 100 | | | | | | | 100 |
| | 250 | | | | | | | | | | | | | 93 | | | | | | | |
| | 63 | | | | | | | | | | | | | | | | | | | | |
| 77 | 1000 | | | | | | | | | | | | | 100 | | | | | | | 100 |
| | 250 | | | | | | | | | | | | | 94 | | | | | | | |
| | 63 | | | | | | | | | | | | | | | | | | | | |
| 78 | 1000 | | | | | | | | | | | | | 100 | | | | | | | 100 |
| | 250 | | | | | | | | | | | | | | | | | | | | |
| | 63 | | | | | | | | | | | | | | | | | | | | |
| 79 | 1000 | | | | | | | | | | | | | 100 | | | | | | | |
| | 250 | | | | | | | | | | | | | 79 | | | | | | | |
| | 63 | | | | | | | | | | | | | | | | | | | | |
| 80 | 1000 | | | | | | | | | | | 100 | | 100 | 100 | | | | | 98 | |
| | 250 | | | | | | | | | | | 79 | | 97 | 95 | | | | | | |
| | 63 | | | | | | | | | | | | | | | | | | | | |
| 81 | 1000 | | | | | | | | | | | 100 | 70 | 100 | 100 | | | | | 98 | |
| | 250 | | | | | | | | | | | 83 | | 89 | 70 | | | | | | |
| | 63 | | | | | | | | | | | | | | | | | | | | |
| 82 | 1000 | | | | | | | | | | | 100 | 80 | 100 | 100 | | | | | 100 | |
| | 250 | | | | | | | | | | | 87 | | 100 | | | | | | | |
| | 63 | | | | | | | | | | | | | | | | | | | | |
| 83 | 1000 | | | | | | | | | | | 100 | | 100 | 100 | | | | | 100 | |
| | 250 | | | | | | | | | | | 90 | | 92 | 80 | | | | | | |
| | 63 | | | | | | | | | | | | | | | | | | | | |
| 84 | 1000 | | | | | | | | | | | 96 | | 100 | 100 | | | | | 100 | |
| | 250 | | | | | | | | | | | | | 93 | 80 | | | | | | |
| | 63 | | | | | | | | | | | 100 | | 100 | 95 | | | | | 100 | |
| | | | | | | | | | | | | | | 96 | | | | | | | |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 85 | 1000 |   |   |   |   |   |   |   |   |   |   | 90 |   |   |   |   |   |   |   | 100 |   |
|    | 250  |   |   |   |   |   |   |   |   |   |   |    |   |   |   |   |   |   |   |     |   |
|    | 63   |   |   |   |   |   |   |   |   |   |   |    |   |   |   |   |   |   |   |     |   |
|    | 16   |   |   |   |   |   |   |   |   |   |   |    |   |   |   |   |   |   |   |     |   |
| 86 | 1000 |   |   |   |   |   |   |   |   |   |   |    |   | 100 |   |   |   |   |   | 100 |   |
|    | 250  |   |   |   |   |   |   |   |   |   |   |    | 70 | 90  |   |   |   |   |   |     |   |
|    | 63   |   |   |   |   |   |   |   |   |   |   |    |   |     |   |   |   |   |   |     |   |
| 87 | 1000 |   |   |   |   |   |   |   |   |   |   | 100 |   | 100 | 100 |   |   |   |   | 100 |   |
|    | 250  |   |   |   |   |   |   |   |   |   |   | 84  |   | 84  | 70  |   |   |   |   |     |   |
|    | 63   |   |   |   |   |   |   |   |   |   |   |     |   |     |     |   |   |   |   |     |   |
| 88 | 1000 |   |   |   |   |   |   |   |   |   |   | 97  |   | 94  | 95  |   |   |   |   | 100 |   |
|    | 250  |   |   |   |   |   |   |   |   |   |   | 73  |   | 76  | 70  |   |   |   |   |     |   |
|    | 63   |   |   |   |   |   |   |   |   |   |   |     |   |     |     |   |   |   |   |     |   |
| 89 | 1000 |   |   |   |   |   |   |   |   |   |   | 100 |   | 100 | 100 |   |   |   |   | 100 |   |
|    | 250  |   |   |   |   |   |   |   |   |   |   | 90  |   | 90  | 90  |   |   |   |   |     |   |
|    | 63   |   |   |   |   |   |   |   |   |   |   |     |   |     |     |   |   |   |   |     |   |
| 90 | 1000 |   |   |   |   |   |   |   |   |   |   | 100 |   | 93  | 100 |   |   |   |   | 100 |   |
|    | 250  |   |   |   |   |   |   |   |   |   |   | 77  |   |     | 95  |   |   |   |   |     |   |
|    | 63   |   |   |   |   |   |   |   |   |   |   |     |   |     | 80  |   |   |   |   |     |   |
|    | 16   |   |   |   |   |   |   |   |   |   |   |     |   |     |     |   |   |   |   |     |   |
| 91 | 1000 |   |   |   |   |   |   |   |   |   |   | 94  |   | 100 | 100 |   |   |   |   | 98  |   |
|    | 250  |   |   |   |   |   |   |   |   |   |   |     |   | 80  | 80  |   |   |   |   |     |   |
|    | 63   |   |   |   |   |   |   |   |   |   |   |     |   |     |     |   |   |   |   |     |   |
| 92 | 1000 |   |   |   |   |   |   |   |   |   |   | 97  |   |     |     |   |   |   |   | 80  |   |
|    | 250  |   |   |   |   |   |   |   |   |   |   | 74  |   |     |     |   |   |   |   |     |   |
|    | 63   |   |   |   |   |   |   |   |   |   |   |     |   |     |     |   |   |   |   |     |   |
| 93 | 1000 |   |   |   |   |   |   | 83 |   |   |   | 100 | 82 | 97  |     |   |   |   |   |     |   |
|    | 250  |   |   |   |   |   |   |    |   |   |   | 84  |   | 93  |     |   |   |   |   |     |   |
|    | 63   |   |   |   |   |   |   |    |   |   |   |     |   | 74  |     |   |   |   |   |     |   |
|    | 16   |   |   |   |   |   |   |    |   |   |   |     |   |     |     |   |   |   |   |     |   |
| 94 | 1000 |   |   |   |   |   |   |    |   |   |   |     |   | 100 |     |   |   |   |   |     | 100 |
|    | 250  |   |   |   |   |   |   |    |   |   |   |     |   | 97  |     |   |   |   |   |     |     |
|    | 63   |   |   |   |   |   |   |    |   |   |   |     |   |     |     |   |   |   |   |     |     |
| 95 | 1000 |   |   |   |   |   |   |    |   |   |   |     |   | 100 |     |   |   |   |   |     | 100 |
|    | 250  |   |   |   |   |   |   |    |   |   |   |     |   | 95  |     |   |   |   |   |     |     |
|    | 63   |   |   |   |   |   |   |    |   |   |   |     |   |     |     |   |   |   |   |     |     |
| 96 | 1000 |   |   |   |   |   |   |    |   |   |   |     |   | 100 |     |   |   |   |   |     | 100 |
|    | 250  |   |   |   |   |   |   |    |   |   |   |     |   | 91  |     |   |   |   |   |     |     |
|    | 63   |   |   |   |   |   |   |    |   |   |   |     |   |     |     |   |   |   |   |     |     |
| 97 | 1000 |   |   |   |   |   |   | 74 |   |   |   |     |   | 100 |     |   |   |   |   |     | 100 |
|    | 250  |   |   |   |   |   |   |    |   |   |   |     |   | 100 |     |   |   |   |   |     |     |
|    | 63   |   |   |   |   |   |   |    |   |   |   |     |   |     |     |   |   |   |   |     |     |
|    | 16   |   |   |   |   |   |   |    |   |   |   |     |   |     |     |   |   |   |   |     |     |
| 98 | 1000 |   |   |   |   |   |   |    |   |   |   |     |   | 100 |     |   |   |   |   |     | 100 |
|    | 250  |   |   |   |   |   |   |    |   |   |   |     |   | 100 |     |   |   |   |   |     |     |
|    | 63   |   |   |   |   |   |   |    |   |   |   |     |   | 72  |     |   |   |   |   |     |     |
| 99 | 1000 |   |   |   |   |   |   | 94 |   |   |   |     |   | 100 | 78  |   |   |   |   |     | 100 |
|    | 250  |   |   |   |   |   |   |    |   |   |   |     |   | 97  |     |   |   |   |   |     |     |
|    | 63   |   |   |   |   |   |   |    |   |   |   |     |   |     |     |   |   |   |   |     |     |
| 100| 1000 |   |   |   |   |   |   |    |   |   |   |     |   | 100 |     |   |   |   |   |     | 100 |
|    |      |   |   |   |   |   |   |    |   |   |   |     |   | 100 |     |   |   |   |   |     |     |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 101 | 250 |   |   |   |   |   |   |   |   |   |   |   |   | 100 |   |   |   |   |   |   | 100 |
|  | 63 |   |   |   |   |   |   |   |   |   |   |   |   | 95 |   |   |   |   |   |   |  |
| 102 | 1000 |   |   |   |   |   |   |   |   |   |   |   |   | 100 |   |   |   |   |   |   | 70 |
|  | 250 |   |   |   |   |   |   |   |   |   |   |   |   | 94 |   |   |   |   |   |   |  |
|  | 63 |   |   |   |   |   |   |   |   |   |   |   |   |   |   |   |   |   |   |   |  |
| 103 | 1000 |   |   |   |   |   |   |   |   |   |   |   |   | 100 |   |   |   |   |   |   | 100 |
|  | 250 |   |   |   |   |   |   |   |   |   |   |   |   | 94 |   |   |   |   |   |   |  |
|  | 63 |   |   |   |   |   |   |   |   |   |   |   |   |   |   |   |   |   |   |   |  |
| 104 | 1000 |   |   |   |   |   |   |   |   |   |   |   |   | 100 |   |   |   |   |   |   | 100 |
|  | 250 |   |   |   |   |   |   |   |   |   |   |   |   | 93 |   |   |   |   |   |   |  |
|  | 63 |   |   |   |   |   |   |   |   |   |   |   |   |   |   |   |   |   |   |   |  |
| 105 | 1000 |   |   |   |   |   |   |   |   |   |   |   |   | 100 |   |   |   |   |   |   | 100 |
|  | 250 |   |   |   |   |   |   |   |   |   |   |   |   | 100 |   |   |   |   |   |   |  |
|  | 63 |   |   |   |   |   |   |   |   |   |   |   |   |   |   |   |   |   |   |   |  |
| 106 | 1000 |   |   |   |   |   |   |   |   |   |   |   |   | 100 |   |   |   |   |   |   | 100 |
|  | 250 |   |   |   |   |   |   |   |   |   |   |   |   | 97 |   |   |   |   |   |   |  |
|  | 63 |   |   |   |   |   |   |   |   |   |   |   |   |   |   |   |   |   |   |   |  |
| 107 | 1000 |   |   |   |   |   |   |   |   |   |   |   |   | 72 |   |   |   |   |   |   | 100 |
|  | 250 |   |   |   |   |   |   |   | 86 |   |   |   |   | 89 |   |   |   |   |   |   |  |
|  | 63 |   |   |   |   |   |   |   |   |   |   |   |   |   |   |   |   |   |   |   |  |
| 108 | 1000 |   |   |   |   |   |   |   |   |   |   |   |   | 93 |   |   |   |   |   |   | 90 |
|  | 250 |   |   |   |   |   |   |   |   |   |   |   |   |   |   |   |   |   |   |   |  |
|  | 63 |   |   |   |   |   |   |   |   |   |   |   |   |   |   |   |   |   |   |   |  |
| 109 | 1000 |   |   |   |   |   |   |   |   |   |   |   |   | 100 |   |   |   |   |   |   | 100 |
|  | 250 |   |   |   |   |   |   |   |   |   |   |   |   | 96 |   |   |   |   |   |   |  |
|  | 63 |   |   |   |   |   |   |   |   |   |   |   |   |   |   |   |   |   |   |   |  |
| 110 | 1000 |   |   |   |   |   |   |   |   |   |   |   |   | 100 |   |   |   |   |   |   | 100 |
|  | 250 |   |   |   |   |   |   |   |   |   |   |   |   | 100 |   |   |   |   |   |   |  |
|  | 63 |   |   |   |   |   |   |   |   |   |   |   |   |   |   |   |   |   |   |   |  |
| 111 | 1000 |   |   |   |   |   |   |   |   |   |   |   |   | 100 |   |   |   |   |   |   | 100 |
|  | 250 |   |   |   |   |   |   |   |   |   |   |   |   | 100 |   |   |   |   |   |   |  |
|  | 63 |   |   |   |   |   |   |   |   |   |   |   |   |   |   |   |   |   |   |   |  |
| 112 | 1000 |   |   |   |   |   |   |   |   |   |   |   |   | 92 |   |   |   |   |   |   | 100 |
|  | 250 |   |   |   |   |   |   |   |   |   |   |   |   |   |   |   |   |   |   |   |  |
|  | 63 |   |   |   |   |   |   |   |   |   |   |   |   |   |   |   |   |   |   |   |  |
| 113 | 1000 |   |   |   |   |   |   |   |   |   |   |   |   | 100 |   |   |   |   |   |   | 100 |
|  | 250 |   |   |   |   |   |   |   |   |   |   |   |   | 91 |   |   |   |   |   |   |  |
|  | 63 |   |   |   |   |   |   |   |   |   |   |   |   |   |   |   |   |   |   |   |  |
| 114 | 1000 |   |   |   |   |   |   |   |   |   |   |   |   | 100 |   |   |   |   |   |   | 100 |
|  | 250 |   |   |   |   |   |   |   |   |   |   |   |   | 90 |   |   |   |   |   |   |  |
|  | 63 |   |   |   |   |   |   |   |   |   |   |   |   |   |   |   |   |   |   |   |  |
| 115 | 1000 |   |   |   |   |   |   |   |   |   |   |   |   | 94 |   |   |   |   |   |   | 90 |
|  | 250 |   |   |   |   |   |   |   |   |   |   |   |   |   |   |   |   |   |   |   | 80 |
|  | 63 |   |   |   |   |   |   |   |   |   |   |   |   |   |   |   |   |   |   |   |  |
|  | 16 |   |   |   |   |   |   |   |   |   |   |   |   |   |   |   |   |   |   |   |  |
| 116 | 1000 |   |   |   |   |   |   |   |   |   |   |   |   | 98 |   |   |   |   |   |   | 80 |
|  | 250 |   |   |   |   |   |   |   |   |   |   |   |   | 79 |   |   |   |   |   |   |  |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 117 | 250 |   |   |   |   |   |   |   |   |   |   |   |   |   |   |   |   |   |   |   | 98 |
|  | 63 |   |   |   |   |   |   |   |   |   |   |   |   |   | 92 |   |   |   |   |   |   |
| 118 | 1000 |   |   |   |   |   |   |   |   |   |   |   |   |   | 90 |   |   |   |   |   |   |
|  | 250 |   |   |   |   |   |   |   |   |   |   |   |   |   |   |   |   |   |   |   |   |
|  | 63 |   |   |   |   |   |   |   |   |   |   |   |   |   |   |   |   |   |   |   |   |
| 119 | 1000 |   |   |   |   |   |   |   |   |   |   |   |   |   |   |   |   |   |   |   | 75 |
|  | 250 |   |   |   |   |   |   |   |   |   |   |   |   |   | 93 |   |   |   |   |   | 75 |
|  | 63 |   |   |   |   |   |   |   |   |   |   |   |   |   |   |   |   |   |   |   |   |
|  | 16 |   |   |   |   |   |   |   |   |   |   |   |   |   |   |   |   |   |   |   |   |
| 120 | 1000 |   |   |   |   |   |   |   |   |   |   |   |   |   | 100 |   |   |   |   |   | 85 |
|  | 250 |   |   |   |   |   |   |   |   |   |   |   |   |   | 88 |   |   |   |   |   |   |
|  | 63 |   |   |   |   |   |   |   |   |   |   |   |   |   |   |   |   |   |   |   |   |
|  | 16 |   |   |   |   |   |   |   |   |   |   |   |   |   |   |   |   |   |   |   |   |
| 121 | 1000 |   |   |   |   |   |   |   |   |   |   |   |   |   | 100 |   |   |   |   |   | 100 |
|  | 250 |   |   |   |   |   |   |   |   |   |   |   |   |   | 91 |   |   |   |   |   |   |
|  | 63 |   |   |   |   |   |   |   |   |   |   |   |   |   |   |   |   |   |   |   |   |
|  | 16 |   |   |   |   |   |   |   |   |   |   |   |   |   |   |   |   |   |   |   |   |
| 122 | 1000 |   |   |   |   |   |   |   |   |   |   |   |   |   | 98 |   |   |   |   |   | 100 |
|  | 250 |   |   |   |   |   |   |   |   |   |   |   |   |   | 78 |   |   |   |   |   | 90 |
|  | 63 |   |   |   |   |   |   |   |   |   |   |   |   |   |   |   |   |   |   |   |   |
|  | 16 |   |   |   |   |   |   |   |   |   |   |   |   |   |   |   |   |   |   |   |   |
| 123 | 1000 |   |   |   |   |   |   |   |   |   |   |   |   |   | 100 |   |   |   |   |   | 100 |
|  | 250 |   |   |   |   |   |   |   |   |   |   |   |   |   | 95 |   |   |   |   |   |   |
|  | 63 |   |   |   |   |   |   |   |   |   |   |   |   |   |   |   |   |   |   |   |   |
|  | 16 |   |   |   |   |   |   |   |   |   |   |   |   |   |   |   |   |   |   |   |   |
| 124 | 1000 |   |   |   |   |   |   |   |   |   |   |   |   |   | 96 |   |   |   |   |   | 100 |
|  | 250 |   |   |   |   |   |   |   |   |   |   |   |   |   |   |   |   |   |   |   |   |
|  | 63 |   |   |   |   |   |   |   |   |   |   |   |   |   |   |   |   |   |   |   |   |
|  | 16 |   |   |   |   |   |   |   |   |   |   |   |   |   |   |   |   |   |   |   |   |
| 125 | 1000 |   |   |   |   |   |   |   |   |   |   |   |   |   | 91 |   |   |   |   |   | 70 |
|  | 250 |   |   |   |   |   |   |   |   |   |   |   |   |   |   |   |   |   |   |   |   |
|  | 63 |   |   |   |   |   |   |   |   |   |   |   |   |   |   |   |   |   |   |   |   |
|  | 16 |   |   |   |   |   |   |   |   |   |   |   |   |   |   |   |   |   |   |   |   |
| 126 | 1000 |   |   |   |   |   |   |   |   |   |   |   |   |   | 97 |   |   |   |   |   | 90 |
|  | 250 |   |   |   |   |   |   |   |   |   |   |   |   |   |   |   |   |   |   |   |   |
|  | 63 |   |   |   |   |   |   |   |   |   |   |   |   |   |   |   |   |   |   |   |   |
|  | 16 |   |   |   |   |   |   |   |   |   |   |   |   |   |   |   |   |   |   |   |   |
| 127 | 1000 |   |   |   |   |   |   |   |   |   |   |   |   |   | 100 |   |   |   |   |   | 80 |
|  | 250 |   |   |   |   |   |   |   |   |   |   |   |   |   | 70 |   |   |   |   |   |   |
|  | 63 |   |   |   |   |   |   |   |   |   |   |   |   |   |   |   |   |   |   |   |   |
|  | 16 |   |   |   |   |   | 76 |   |   |   |   |   |   |   |   |   |   |   |   |   |   |
| 128 | 1000 |   |   |   |   |   |   |   |   |   |   |   |   |   | 96 |   |   |   |   |   | 98 |
|  | 250 |   |   |   |   |   |   |   |   |   |   |   |   |   |   |   |   |   |   |   | 80 |
|  | 63 |   |   |   |   |   |   |   |   |   |   |   |   |   |   |   |   |   |   |   |   |
|  | 16 |   |   |   |   |   |   |   |   |   |   |   |   |   |   |   |   |   |   |   |   |
| 129 | 1000 |   |   |   |   |   |   |   |   |   |   |   |   |   | 100 |   |   |   |   |   | 90 |
|  | 250 |   |   |   |   |   |   |   |   |   |   |   |   |   |   |   |   |   |   |   | 80 |
|  | 63 |   |   |   |   |   |   |   |   |   |   |   |   |   |   |   |   |   |   |   | 95 |
|  | 16 |   |   |   |   |   |   |   |   |   |   |   |   |   |   |   |   |   |   |   | 80 |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 130 | 1000 |   |   |   |   |   |   |   |   |   |   |   |   | 92 |   |   |   |   |   |   | 95 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 131 | 1000 |   |   |   |   |   |   |   |   |   |   |   |   | 98 |   |   |   |   |   |   | 90 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 132 | 1000 |   |   |   |   |   |   |   |   |   |   |   |   | 97 |   |   |   |   |   |   | 100 |
|   | 250 |   |   |   |   |   |   |   |   |   |   |   |   | 81 |   |   |   |   |   |   |   |
|   | 63 |   |   |   |   |   |   |   |   |   |   |   |   |   |   |   |   |   |   |   |   |
|   | 16 |   |   |   |   |   |   |   |   |   |   |   |   |   |   |   |   |   |   |   |   |
| 133 | 1000 |   |   |   |   |   |   |   |   |   |   |   |   | 88 |   |   |   |   |   |   | 80 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 134 | 1000 |   |   |   |   |   |   |   |   |   |   |   |   | 97 |   |   |   |   |   |   | 100 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 135 | 1000 |   |   |   |   |   |   |   |   |   |   |   |   | 97 |   |   |   |   |   |   | 100 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 136 | 1000 |   |   |   |   |   |   |   |   |   |   |   |   | 89 |   |   |   |   |   |   | 80 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 137 | 1000 |   |   |   |   |   |   |   |   |   |   |   |   | 92 |   |   |   |   |   |   | 92 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 138 | 1000 |   |   |   |   |   |   |   |   |   |   |   |   | 82 |   |   |   |   |   |   | 100 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 139 | 1000 |   |   |   |   |   |   |   |   |   |   |   |   | 81 |   |   |   |   |   |   | 100 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 140 | 1000 |   |   |   |   |   |   |   |   |   |   |   |   | 81 |   |   |   |   |   |   | 100 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 141 | 1000 |   |   |   |   |   |   |   |   |   |   |   |   |   |   |   |   |   |   |   | 100 |
|   | 250 |   |   |   |   |   |   |   |   |   |   |   |   |   |   |   |   |   |   |   |   |
| 142 | 1000 |   |   |   |   |   |   |   |   |   |   |   |   |   |   |   |   |   |   |   | 100 |
|   | 250 |   |   |   |   |   |   |   |   |   |   |   |   |   |   |   |   |   |   |   |   |
| 143 | 1000 |   |   |   |   |   |   |   |   |   |   |   |   |   |   |   |   |   |   |   | 100 |
|   | 250 |   |   |   |   |   |   |   |   |   |   |   |   |   |   |   |   |   |   |   |   |
| 144 | 1000 |   |   |   |   |   |   |   |   |   |   |   |   | 81 |   |   |   |   |   |   | 100 |
|   | 250 |   |   |   |   |   |   |   |   |   |   |   |   |   |   |   |   |   |   |   |   |
|   | 63 |   |   |   |   |   |   |   |   |   |   |   |   |   |   |   |   |   |   |   |   |
| 145 | 1000 |   |   |   |   |   |   |   |   |   |   |   |   | 93 |   |   |   |   |   |   | 100 |
|   | 250 |   |   |   |   |   |   |   |   |   |   |   |   | 76 |   |   |   |   |   |   |   |
|   | 63 |   |   |   |   |   |   |   |   |   |   |   |   |   |   |   |   |   |   |   |   |
|   | 16 |   |   |   |   |   |   |   |   |   |   |   |   |   |   |   |   |   |   |   |   |
| 146 | 1000 |   |   |   |   |   |   |   |   |   |   |   |   | 100 |   |   |   |   |   |   | 100 |
|   | 250 |   |   |   |   |   |   |   |   |   |   |   |   |   |   |   |   |   |   |   |   |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 147 | 63 | | | | | | | | | | | | | 96 | | | | | | | |
| 148 | 1000 | | | | | | | | | | | | | 98 | | | | | | | |
|  | 250 | | | | | | | | | | | | | | | | | | | | 100 |
|  | 63 | | | | | | | | | | | | | | | | | | | | |
| 149 | 1000 | | | | | | | | | | | | | 97 | | | | | | | |
|  | 250 | | | | | | | | | | | | | | | | | | | | 100 |
|  | 63 | | | | | | | | | | | | | | | | | | | | |
| 150 | 1000 | 100 | | | | | | | | | | | | 91 | | | | | | | |
|  | 250 | 75 | 90 | | | | | | | | | | | | | | | | | | 100 |
|  | 63 | | | | | | | | | | | | | | | | | | | | |
|  | 16 | | | | | | | | | | | | | | | | | | | | |
| 151 | 1000 | 100 | | | | | | 100 | | | 100 | | | 100 | | | | | | | |
|  | 250 | | | | | | | 100 | | | 100 | | | 100 | | | | | | | |
|  | 63 | | | | | | | 91 | | | 100 | | | 94 | | | | | | | |
|  | 16 | | | | | | | | | | 97 | | | | | | | | | | |
| 152 | 1000 | 80 | | | | | | | 100 | | 100 | | | 100 | | | | | | | |
|  | 250 | | | | | | | | 100 | | 100 | | | 100 | | | | | | | |
|  | 63 | | | | | | | | 93 | | 97 | | | 97 | | | | | | | |
|  | 16 | | | | | | | | | | | | | | | | | | | | |
| 153 | 1000 | 90 | | | | | | 100 | | | 100 | | 82 | | | | | | | | |
|  | 250 | | | | | | | | | | 74 | | | | | | | | | | |
|  | 63 | | | | | | | | | | | | | | | | | | | | |
|  | 16 | | | | | | | | | | | | | | | | | | | | |
| 154 | 1000 | | | | | | | 100 | | | 100 | | 100 | | | | | | | | |
|  | 250 | | | | | | | | | | 94 | | | | | | | | | | |
|  | 63 | | | | | | | | | | | | | | | | | | | | |
|  | 16 | | | | | | | | | | | | | | | | | | | | |
| 155 | 1000 | | | | | | | | | | | | | 97 | 94 | | | | | | |
|  | 250 | | | | | | | | | | | | | 76 | | | | | | | |
|  | 63 | | | | | | | | | | | | | | | | | | | | |
|  | 16 | | | | | | | | | | | | | | | | | | | | |
| 156 | 1000 | | | | | | | | | | | | | 100 | | | | | | | 99 |
|  | 250 | | | | | | | | | | | | | 90 | | | | | 100 | | |
|  | 63 | | | | | | | | | | | | | | | | | | | | |
|  | 16 | | | | | | | | | | | | | | | | | | | | |
| 157 | 1000 | | | | | | | | | | 100 | | 100 | 100 | | | | | | | 100 |
|  | 250 | | | | | | | | | | 100 | | | 93 | | | | | 100 | | |
|  | 63 | | | | | | | | | | | | | | | | | | | | |
|  | 16 | | | | | | | | | | | | | | | | | | | | |
| 158 | 1000 | 45 | | | | | | 100 | | | 100 | | 91 | 100 | 100 | | | | | | |
|  | 250 | 100 | | | | | | | | | 100 | | | 97 | 95 | | | | 100 | | |
|  | 63 | | | | | | | | | | 97 | | | | | | | | 100 | | |
|  | 16 | | | | | | | | | | 81 | | | | | | | | | | |
| 159 | 1000 | | | | | | | | | | 100 | | | 100 | | | | | | | |
|  | 250 | | | | | | | | | | 94 | | | 96 | | | | | 100 | | |
|  | 63 | | | | | | | | | | | | | | | | | | | | |
|  | 16 | | | | | | | | | | | | | | | | | | | | |
| 160 | 1000 | 90 | | | | | | 100 | | | | | | | | | | | 100 | | |
|  | 250 | | | | | | | | | | | | | | | | | | | | |
|  | 63 | | | | | | | | | | | | | | | | | | | | |
| 161 | 1000 | 100 | | | | | | | | | 100 | | | 97 | | | | | | | |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 162 | 250 |  | 70 |  |  |  |  |  |  |  |  |  |  |  |  |  |  |  |  |  |  |
|  | 63 |  |  |  |  |  |  |  |  |  |  |  |  |  |  |  |  |  |  |  |  |
|  | 16 |  |  |  |  |  |  |  |  |  |  |  |  |  |  |  |  |  |  |  |  |
| 163 | 1000 | 100 |  |  |  |  |  |  |  |  |  | 100 |  | 100 |  |  |  |  |  |  |  |
|  | 250 | 70 |  |  |  |  |  |  |  |  |  | 97 |  | 100 |  |  |  |  |  |  |  |
|  | 63 |  |  |  |  |  |  |  |  |  |  | 83 |  | 86 |  |  |  |  |  |  |  |
|  | 16 |  |  |  |  |  |  |  |  |  |  |  |  |  |  |  |  |  |  |  |  |
| 164 | 1000 |  |  |  |  |  |  |  |  |  |  | 100 |  | 100 |  |  |  |  |  |  |  |
|  | 250 |  |  |  |  |  |  |  |  |  |  | 100 |  | 100 |  |  |  |  |  |  |  |
|  | 63 |  |  |  |  |  |  |  |  |  |  | 73 |  | 81 |  |  |  |  |  |  |  |
|  | 16 |  |  |  |  |  |  |  |  |  |  |  |  |  |  |  |  |  |  |  |  |
| 165 | 1000 |  |  |  |  |  |  |  |  |  |  |  |  | 100 |  |  |  |  |  |  | 80 |
|  | 250 |  |  |  |  |  |  |  |  |  |  |  |  | 83 |  |  |  |  |  |  |  |
|  | 63 |  |  |  |  |  |  |  |  |  |  |  |  |  |  |  |  |  |  |  |  |
|  | 16 |  |  |  |  |  |  |  |  |  |  |  |  |  |  |  |  |  |  |  |  |
| 166 | 1000 |  |  |  |  |  |  |  |  |  |  |  |  | 100 |  |  |  |  |  |  | 100 |
|  | 250 |  |  |  |  |  |  |  |  |  |  |  |  | 71 |  |  |  |  |  |  |  |
|  | 63 |  |  |  |  |  |  |  |  |  |  |  |  |  |  |  |  |  |  |  |  |
|  | 16 |  |  |  |  |  |  |  |  |  |  |  |  |  |  |  |  |  |  |  |  |
| 167 | 1000 |  |  |  |  |  |  |  |  |  |  |  |  | 100 |  |  |  |  |  |  | 100 |
|  | 250 |  |  |  |  |  |  |  |  |  |  |  |  |  |  |  |  |  |  |  |  |
|  | 63 |  |  |  |  |  |  |  |  |  |  |  |  |  |  |  |  |  |  |  |  |
|  | 16 |  |  |  |  |  |  |  |  |  |  |  |  |  |  |  |  |  |  |  |  |
| 168 | 1000 |  |  |  |  |  |  | 86 |  |  |  |  |  | 96 |  |  |  |  |  |  | 100 |
|  | 250 |  |  |  |  |  |  |  |  |  |  |  |  | 87 |  |  |  |  |  |  |  |
|  | 63 |  |  |  |  |  |  |  |  |  |  |  |  |  |  |  |  |  |  |  |  |
|  | 16 |  |  |  |  |  |  |  |  |  |  |  |  |  |  |  |  |  |  |  |  |
| 169 | 1000 |  |  |  |  |  |  |  |  |  |  |  |  | 100 |  |  |  |  |  |  | 100 |
|  | 250 |  |  |  |  |  |  |  |  |  |  |  |  | 82 |  |  |  |  |  |  |  |
|  | 63 |  |  |  |  |  |  |  |  |  |  |  |  |  |  |  |  |  |  |  |  |
|  | 16 |  |  |  |  |  |  |  |  |  |  |  |  |  |  |  |  |  |  |  |  |
| 170 | 1000 |  |  |  |  |  |  |  |  |  |  |  |  | 100 |  |  |  |  |  |  | 100 |
|  | 250 |  |  |  |  |  |  |  |  |  |  |  |  | 90 |  |  |  |  |  |  |  |
|  | 63 |  |  |  |  |  |  |  |  |  |  |  |  |  |  |  |  |  |  |  |  |
|  | 16 |  |  |  |  |  |  |  |  |  |  |  |  |  |  |  |  |  |  |  |  |
| 171 | 1000 | 95 |  |  |  |  |  | 81 |  |  |  |  |  | 90 |  |  |  |  |  |  | 100 |
|  | 250 |  |  |  |  |  |  |  |  |  |  |  |  |  |  |  |  |  |  |  |  |
|  | 63 |  |  |  |  |  |  |  |  |  |  |  |  |  |  |  |  |  |  |  |  |
|  | 16 |  |  |  |  |  |  |  |  |  |  |  |  |  |  |  |  |  |  |  |  |
| 172 | 1000 | 90 |  |  |  |  |  |  |  |  |  |  |  | 97 |  |  |  |  |  |  | 97 |
|  | 250 |  |  |  |  |  |  |  |  |  |  |  |  | 72 |  |  |  |  |  |  |  |
|  | 63 |  |  |  |  |  |  |  |  |  |  |  |  |  |  |  |  |  |  |  |  |
|  | 16 |  |  |  |  |  |  |  |  |  |  |  |  |  |  |  |  |  |  |  |  |
| 173 | 1000 | 80 |  |  |  |  |  |  |  |  |  |  |  | 96 |  |  |  |  |  |  | 100 |
|  | 250 |  |  |  |  |  |  |  |  |  |  |  |  | 100 |  |  |  |  |  |  |  |
|  | 63 |  |  |  |  |  |  |  |  |  |  |  |  | 94 |  |  |  |  |  |  |  |
|  | 16 |  |  |  |  |  |  |  |  |  |  |  |  |  |  |  |  |  |  |  |  |
| 174 | 1000 |  |  |  |  |  |  | 100 |  |  |  |  |  | 100 |  |  |  |  |  |  | 100 |
|  | 250 |  |  |  |  |  |  |  |  |  |  |  |  | 72 |  |  |  |  |  |  |  |
|  | 63 |  |  |  |  |  |  |  |  |  |  |  |  |  |  |  |  |  |  |  |  |
|  | 16 |  |  |  |  |  |  |  |  |  |  |  |  |  |  |  |  |  |  |  |  |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 175 | 1000 | | | | | | | 100 | | | | | | | | | | | | | 100 |
|  | 250 | | | | | | | | | | | | | | | | | | | | |  |
|  | 63 | | | | | | | | | | | | | | 91 | | | | | | | 100 |
| 176 | 1000 | 90 | | | | | | | | | | | | | | | | | | | |  |
|  | 250 | | | | | | | | | | | | | | 97 | | | | | | |  |
|  | 63 | | | | | | | | | | | | | | 76 | | | | | | | 100 |
|  | 16 | | | | | | | | | | | | | | | | | | | | |  |
| 210 | 1000 | | | | | | | | | | | | | | 85 | | | | | | | 95 |
|  | 250 | | | | | | | | | | | | | | | | | | | | | 70 |
|  | 63 | | | | | | | | | | | | | | | | | | | | |  |
| 211 | 1000 | | | | | | | | | | | | | | 78 | | | | | | | 95 |
|  | 250 | | | | | | | | | | | | | | | | | | | | | 70 |
|  | 63 | | | | | | | | | | | | | | | | | | | | |  |
| 212 | 1000 | | | | | | | | | | | | | | | | | | | | | 100 |
|  | 250 | | | | | | | | | | | | | | | | | | | | |  |
|  | 63 | | | | | | | | | | | | | | | | | | | | |  |
| 213 | 1000 | | | | | | | | | | | | | | 77 | | | | | | | 100 |
|  | 250 | | | | | | | | | | | | | | | | | | | | |  |
|  | 63 | | | | | | | | | | | | | | | | | | | | |  |
| 214 | 1000 | | | | | | | | | | | | | | 95 | | | | | | | 100 |
|  | 250 | | | | | | | | | | | | | | 70 | | | | | | |  |
|  | 63 | | | | | | | | | | | | | | | | | | | | |  |
|  | 16 | | | | | | | | | | | | | | | | | | | | |  |
| 216 | 1000 | | | | | | | | | | | | | | 95 | | | | | | | 100 |
|  | 250 | | | | | | | | | | | | | | | | | | | | |  |
|  | 63 | | | | | | | | | | | | | | | | | | | | |  |
| 217 | 1000 | | | | | | | | | | | | | | 93 | | | | | | | 100 |
|  | 250 | | | | | | | | | | | | | | | | | | | | |  |
|  | 63 | | | | | | | | | | | | | | | | | | | | |  |
| 218 | 1000 | | | | | | | | | | | | | | 84 | | | | | | | 100 |
|  | 250 | | | | | | | | | | | | | | | | | | | | |  |
|  | 63 | | | | | | | | | | | | | | | | | | | | |  |
| 219 | 1000 | | | | | | | 85 | | | | | | | 95 | | | | | | | 80 |
|  | 250 | | | | | | | | | | | | | | | | | | | | |  |
|  | 63 | | | | | | | | | | | | | | | | | | | | |  |
|  | 16 | | | | | | | | | | | | | | | | | | | | |  |
| 220 | 1000 | | | | | | | 100 | | | | | | | 100 | 76 | | | | | | 100 |
|  | 250 | | | | | | | | | | | | | | 97 | | | | | | |  |
|  | 63 | | | | | | | | | | | | | | | | | | | | |  |
|  | 16 | | | | | | | | | | | | | | | | | | | | |  |
| 221 | 1000 | | | | | | | 92 | | | | | | | 100 | | | | | | | 100 |
|  | 250 | | | | | | | | | | | | | | 93 | | | | | | |  |
|  | 63 | | | | | | | | | | | | | | | | | | | | |  |
|  | 16 | | | | | | | | | | | | | | | | | | | | |  |
| 222 | 1000 | | | | | | | 100 | | | | | | | 100 | 88 | | | | | | 100 |
|  | 250 | | | | | | | | | | | | | | 97 | | | | | | |  |

TABLE 2-continued

| Compound No. | Concentration (ppm) | A | C | D | E | G | H | I | J | K | L | M | N | O | P | Q | R | T | W | X | Y |
|---|---|---|---|---|---|---|---|---|---|---|---|---|---|---|---|---|---|---|---|---|---|
| 225 | 63 |   |   |   |   |   |   |   |   |   |   |   |   | 100 |   |   |   |   |   |   |   |
|     | 16 |   |   |   |   |   |   |   |   |   |   |   |   | 84 |   |   |   |   |   |   |   |
| 226 | 1000 |   |   |   |   |   |   | 83 |   |   |   |   |   |   |   |   |   |   |   |   | 100 |
|     | 250 |   |   |   |   |   |   |   |   |   |   |   |   | 100 |   |   |   |   |   |   |   |
|     | 63 |   |   |   |   |   |   |   |   |   |   |   |   | 93 |   |   |   |   |   |   |   |
|     | 16 |   |   |   |   |   |   |   |   |   |   |   |   |   | 79 |   |   |   |   |   |   |
| 227 | 1000 |   |   |   |   |   |   | 86 |   |   |   |   |   |   |   |   |   |   |   |   | 100 |
|     | 250 |   |   |   |   |   |   |   |   |   |   |   |   | 100 |   |   |   |   |   |   |   |
|     | 63 |   |   |   |   |   |   |   |   |   |   |   |   | 97 |   |   |   |   |   |   |   |
|     | 16 |   |   |   |   |   |   |   |   |   |   |   |   |   |   |   |   |   |   |   |   |
| 228 | 1000 |   |   |   |   |   |   | 100 |   |   |   |   |   |   |   |   |   |   |   |   | 100 |
|     | 250 |   |   |   |   |   |   |   |   |   |   |   |   | 100 |   |   |   |   |   |   |   |
|     | 63 |   |   |   |   |   |   |   |   |   |   |   |   | 76 |   |   |   |   |   |   |   |
|     | 16 |   |   |   |   |   |   |   |   |   |   |   |   |   |   |   |   |   |   |   |   |
| 229 | 1000 |   |   |   |   |   |   | 100 |   |   |   |   |   |   |   |   |   |   |   |   | 100 |
|     | 250 |   |   |   |   |   |   |   |   |   |   |   |   | 92 |   |   |   |   |   |   |   |
|     | 63 |   |   |   |   |   |   |   |   |   |   |   |   |   |   |   |   |   |   |   |   |
|     | 16 |   |   |   |   |   |   |   |   |   |   |   |   |   |   |   |   |   |   |   |   |
| 230 | 1000 |   |   |   |   |   |   | 100 |   |   |   |   |   |   |   |   |   |   |   |   | 100 |
|     | 250 |   |   |   |   |   |   |   |   |   |   |   |   | 93 |   |   |   |   |   |   |   |
|     | 63 |   |   |   |   |   |   |   |   |   |   |   |   |   |   |   |   |   |   |   |   |
|     | 16 |   |   |   |   |   |   |   |   |   |   |   |   |   |   |   |   |   |   |   |   |
| 231 | 1000 | 100 |   |   |   |   |   | 100 |   |   |   |   |   |   | 100 |   |   |   |   |   |   |
|     | 250 |   |   |   |   |   |   |   |   |   |   |   |   | 100 |   |   |   |   |   |   |   |
|     | 63 |   |   |   |   |   |   |   |   |   |   |   |   | 93 |   |   |   |   |   |   |   |
|     | 16 |   |   |   |   |   |   |   |   |   |   |   |   |   |   |   |   |   |   |   |   |
| 232 | 1000 | 100 |   |   |   |   |   | 100 |   |   |   |   |   |   |   |   |   |   |   |   | 100 |
|     | 250 |   |   |   |   |   |   |   |   |   |   |   |   | 100 |   |   |   |   |   |   |   |
|     | 63 |   |   |   |   |   |   |   |   |   |   |   |   | 96 |   |   |   |   |   |   |   |
|     | 16 |   |   |   |   |   |   |   |   |   |   |   |   |   | 98 |   |   |   |   |   |   |
| 233 | 1000 | 100 |   |   |   |   |   |   |   |   |   |   |   |   |   |   |   |   |   |   |   |
|     | 250 |   |   |   |   |   |   |   |   |   |   |   |   | 100 |   |   |   |   |   |   |   |
|     | 63 |   |   |   |   |   |   |   |   |   |   |   |   | 96 |   |   |   |   |   |   |   |
|     | 16 |   |   |   |   |   |   |   |   |   |   |   |   |   | 100 |   |   |   |   |   |   |
| 234 | 1000 | 100 |   |   |   |   |   |   |   |   |   |   |   |   |   |   |   |   |   |   | 100 |
|     | 250 |   |   |   |   |   |   |   |   |   |   |   |   | 100 |   |   |   |   |   |   |   |
|     | 63 |   |   |   |   |   |   |   |   |   |   |   |   | 96 |   |   |   |   |   |   |   |
|     | 16 |   |   |   |   |   |   |   |   |   |   |   |   |   | 92 |   |   |   |   |   |   |
| 235 | 1000 | 100 |   |   |   |   |   |   |   |   |   |   |   |   |   |   |   |   |   |   | 100 |
|     | 250 |   |   |   |   |   |   |   |   |   |   |   |   | 100 |   |   |   |   |   |   |   |
|     | 63 |   |   |   |   |   |   |   |   |   |   |   |   | 96 |   |   |   |   |   |   |   |
|     | 16 |   |   |   |   |   |   |   |   |   |   |   |   |   | 91 |   |   |   |   |   |   |
| 236 | 1000 | 90 |   |   |   |   |   | 100 |   |   |   |   |   |   |   |   |   |   |   |   | 100 |
|     | 250 |   |   |   |   |   |   |   |   |   |   |   |   | 100 |   |   |   |   |   |   |   |
|     | 63 |   |   |   |   |   |   |   |   |   |   |   |   | 86 |   |   |   |   |   |   |   |
|     | 16 |   |   |   |   |   |   |   |   |   |   |   |   |   |   |   |   |   |   |   |   |
| 237 | 1000 | 90 |   |   |   |   |   | 100 |   |   |   |   |   |   |   |   |   |   |   |   | 100 |
|     | 250 |   |   |   |   |   |   |   |   |   |   |   |   | 100 |   |   |   |   |   |   |   |
|     | 63 |   |   |   |   |   |   |   |   |   |   |   |   | 90 |   |   |   |   |   |   |   |
|     | 16 |   |   |   |   |   |   |   |   |   |   |   |   |   |   |   |   |   |   |   |   |

What is claimed is:

1. A compound of the formula:

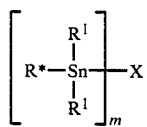 (I)

in which $R^1$ represents alkyl, cyclohexyl or neophyl, $R^*$ represents fluorophenyl or trifluoromethylphenyl when $R^1$ is alkyl; $R^*$ represents neopentyl, trimethylsilylmethyl or dimethylphenylsilylmethyl when $R^1$ is cyclohexyl; or $R^*$ represents 2-thienyl, 3-thienyl, neopentyl, trimethylsilylmethyl, dimethylphenylsilylmethyl or a group of the formula:

wherein $R^3$, $R^4$ and $R^5$ independently represent hydrogen, halogen, trifluoromethyl, lower alkyl or lower alkoxy when $R^1$ is neophyl, m represents 1 or 2, and X represents, when m is 1, halogen, imidazolyl, triazolyl, phenylthio or a radical selected from the group consisting of:

$-OCOR^6$, $-SSCNR^7R^8$, $-NCO$, $-NCS$,

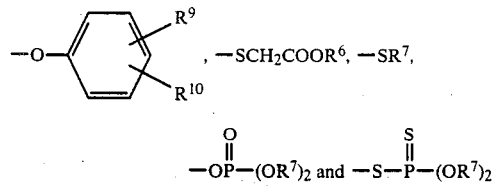, $-SCH_2COOR^6$, $-SR^7$,

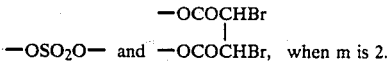

wherein $R^6$ represents alkyl, $R^7$ and $R^8$ independently represent lower alkyl and $R^9$ and $R^{10}$ independently represent hydrogen or lower alkyl; or X represents oxygen, sulfur or a radical selected from:

$$-OSO_2O- \text{ and } -OCOCHBr\overset{|}{-OCOCHBr}, \text{ when m is 2.}$$

2. A pesticidal composition which comprises as an essential component the compound of the formula (I) as defined in claim 1 together with a suitable carrier or adjuvant.

* * * * *